(12) United States Patent
Sherley

(10) Patent No.: US 9,081,008 B2
(45) Date of Patent: Jul. 14, 2015

(54) DETECTING AND COUNTING TISSUE—SPECIFIC STEM CELLS AND USES THEREOF

(75) Inventor: James L. Sherley, Boston, MA (US)

(73) Assignee: James Sherley, Boston, MA (US)

( * ) Notice: Subject to any disclaimer, the term of this patent is extended or adjusted under 35 U.S.C. 154(b) by 328 days.

(21) Appl. No.: 13/513,289

(22) PCT Filed: Dec. 3, 2010

(86) PCT No.: PCT/US2010/058941
§ 371 (c)(1),
(2), (4) Date: Aug. 13, 2012

(87) PCT Pub. No.: WO2011/069093
PCT Pub. Date: Jun. 9, 2011

(65) Prior Publication Data
US 2013/0004965 A1    Jan. 3, 2013

Related U.S. Application Data

(60) Provisional application No. 61/283,485, filed on Dec. 4, 2009, provisional application No. 61/400,087, filed on Jul. 22, 2010.

(51) Int. Cl.
*G01N 33/569* (2006.01)
*G01N 33/50* (2006.01)

(52) U.S. Cl.
CPC ...... *G01N 33/56966* (2013.01); *G01N 33/5073* (2013.01); *G01N 33/5076* (2013.01)

(58) Field of Classification Search
USPC .......... 435/2, 6, 7.1, 373, 374, 376; 436/517, 436/63; 530/358
See application file for complete search history.

(56) References Cited

U.S. PATENT DOCUMENTS

| 7,883,891 B2 * | 2/2011 | Sherley et al. ............... 435/366 |
| 2009/0142760 A1 * | 6/2009 | Sherley et al. ............... 435/6 |

FOREIGN PATENT DOCUMENTS

WO    02/057430 A2    7/2002

OTHER PUBLICATIONS

Chamberlain, et al, "Murine Mesenchymal Stem Cells Exhibit a Restricted Repertoire of Functional Chemokine Receptors: Comparison with Human", PLoS One, vol. 3, Issue 8, pp. 1-6, 2008.
(Continued)

*Primary Examiner* — Gail R Gabel
(74) *Attorney, Agent, or Firm* — Nixon Peabody LLP; Ronald I. Eisenstein; Candace M. Summerford

(57) ABSTRACT

This invention provides methods of determining the number and percent of tissue specific stem cells (TSSCs) in a sample of cells, a population of cells or a sample of tissue. The methods rely on detecting the pattern-specific asymmetric localization of asymmetric self-renewal associated (ASRA) proteins or cell cycle specific proteins (CSSP) in cell undergoing asymmetrical self-renewal, which is a characteristic of TSSCs. The methods can be applied to any situations in which the percent of TSSC is desired such as laboratory research on adult stem cells, in drug development tests, prognostic indicator and therapeutic index, as a diagnostic and prognostic indicator and in monitoring TSSC expansion, e.g., in cell manufacturing processes.

13 Claims, 9 Drawing Sheets

(56) References Cited

OTHER PUBLICATIONS

Creyghton et al, "H2AZ Is Enriched at Polycomb Complex Target Genes in ES Cells and Is Necessary for Lineage Commitment", Cell, vol. 135, pp. 649-661, 2008.

Sherley, James L., "Asymmetric Cell Kinetics Genes: The Key to Expansion of Adult Stem Cells in Culture", Stem Cells, vol. 20, pp. 561-572, 2002.

Huh, Y.H. et al., "Molecular Cloaking of H2A.Z on Mortal DNA Chromosomes During Nonrandom Segregation", Stem Cells, Sep. 2011, vol. 29, pp. 1620-1627.

Huh, Y.H. et al., "SACK-Expanded Hair Follicle Stem Cells Display Asymmetric Nuclear Lgr5 Expression With Non-Random Sister Chromatid Segregation", Scientific Reports, Nov. 2011, vol. 1, Issue 176, pp. 1-9.

Noh, M. et al., "A Resource for Discovering Specific and Universal Biomarkers for Distributed Stem Cells", PLoS One, Jul. 2011, vol. 6, Issue 7, e22077.

Taghizadeh, R. et al., "CXCR6, a Newly Defined Biomarker of Tissue-Specific Stem Cell Asymmetric Self-Renewal, Identifies More Aggressive Human Melanoma Cancer Stem Cells", PLoS One, Dec. 2010, vol. 5, Issue 12, e15183.

\* cited by examiner ially and cycling transiently# DETECTING AND COUNTING TISSUE—SPECIFIC STEM CELLS AND USES THEREOF

CROSS REFERENCE TO RELATED APPLICATIONS

This application is a 35 U.S.C. §371 National Phase Entry Application of International Application No. PCT/US2010/058941, filed Dec. 3, 2010, which designates the United States, and which claims benefit under 35 U.S.C. §119(e) of the U.S. provisional application No. 61/283,485 filed Dec. 4, 2009 and No. 61/400,087 filed Jul. 22, 2010, the contents of which are incorporated herein by reference in their entireties.

GOVERNMENT SUPPORT

This invention was made with Government support under contract No. DPI-OD000805 awarded by the National Institutes of Health. The Government has certain rights in the invention.

BACKGROUND OF INVENTION

Tissue specific stem cells (TSSCs) are rare precursor cells in adult tissues that divide to produce progeny cells that mature into functional tissue cells. In this way, adult stem cells function to replenish mature tissue cells that have expired or to repair tissues and organs that are diseased or damaged. These natural restorative properties make adult stem cells attractive for development for use in gene therapy and cell replacement therapy.

To perform their tissue renewal functions, stem cells must produce differentiating cells while simultaneously maintaining their own undifferentiated, proliferative state. This essential adult stem cell property, called asymmetric cell kinetics (also known as asymmetric self-renewal), is also a major barrier to the detection, counting, expansion and isolation of these cells in culture or in a population of cells derived from a primary tissue. The reason for this difficulty is that in propagating TSSCs in culture and during proliferation, TSSCs are lost in the sea of differentiating cells that they produce. Methods that facilitated effective and accurate estimation of the number of TSSCs in a population of proliferating cells would aid in research and development of gene therapy and cell replacement therapy that uses TSSCs.

Several methods are available for detecting and counting TSSCs. For example, Lee et al., (2003, Biotechnol. Bioeng. 2003, 83:760-71) describes a method for expanding and quantifying TSSCs ex vivo, based on their unique property of asymmetric self-renewal. When TSSCs undergo asymmetric self-renewal, their divisions produce another actively cycling TSSC and a non-stem sister cell. The non-stem sister cell undergoes differentiation, which in culture is often accompanied by cell cycle arrest. The asymmetry for cell cycle transit by the TSSC sister and the non-stem sister cell can be scored by pulse-labeling the paired cells with the thymidine analogue bromodeoxyuridine (BrdU). Since the stem cell sister continues through S-phase, it incorporates BrdU; but the non-stem sister arrests in G1 phase before S phase, and, therefore, does not incorporate BrdU. The asymmetric pattern of sister cell BrdU uptake is specific for the division of asymmetrically self-renewing TSSCs. Both symmetrically self-renewing TSSCs (which occur during body maturation and potentially during wound repair) and symmetrically cycling transiently amplifying, differentiating cells show symmetric patterns of BrdU uptake, with both sisters being BrdU(+). Therefore, this method is not applicable to symmetrically self-renewing TSSCs.

Incorporated BrdU is detected by conventional in situ immunofluorescence (ISIF) with fluorescently tagged BrdU-specific antibodies or by visualizing the quenched fluorescence of DNA dyes like Hoechst. This "sister pair analysis" (SPA or SP) requires that cells are evaluated at cell densities that are sufficiently low to allow verification of sister-sister relationships. Therefore, SPA is not applicable at the high cell densities needed to investigate TSSCs in heterogeneous tissue cell preparations. Moreover, the use of cytochalasin D to trap sister nuclei in the same cytoplasm to verify their sister-sister relationship at high cell densities, as used in the U.S. Patent Application No. 2005/0074874, is not applicable for BrdU-SPA because asymmetric BrdU uptake is lost in cytochalasin D-arrested binucleates.

The U.S. Patent Application No. 2005/0074874 describes the use of immortal DNA strand co-segregation (IDSC) as a specific indicator of TSSCs. It scores the ability of TSSCs to continuously co-segregate chromosomes that bear their oldest DNA strands. This method does make use of cytochalasin D to verify sister-sister relationships even at high cell densities. In this case, BrdU is introduced into TSSC nuclear DNA according to either of two strategies before cells are treated with cytochalasin D. In the "label-exclusion" strategy, it is incorporated into all DNA strands except the immortal DNA strands as TSSCs undergo continuous asymmetric self-renewal. In the "label-retention" strategy, it is first incorporated into "pre-immortal DNA strands" when TSSCs either undergo physiological symmetric self-renewal or are induced to undergo symmetric self-renewal (during which chromosome segregation is random). Thereafter, BrdU-labeled cells are evaluated after a switch to asymmetric self-renewal for a BrdU-free chase. Thereafter, treatment of cells in either strategy with cytochalasin D yields binucleated cells with the BrdU-asymmetry signature of TSSCs. However, this method is not applicable in situations where TSSCs fail to exhibit IDSC.

Merok et al., 2002 (Cancer Res. 2002, 62:6791-5) and Rambhatla et al., 2005 (Cancer Res. 2005, 65:3155-61) both described similar methods to that of the U.S. Application No. 2005/0074874. In the former case, the TSSC nucleus has half the BrdU content of the non-stem sister nucleus; and in the latter case, the TSSC nucleus is the only nucleus that contains BrdU. A shortcoming of this "BrdU-Cyto D" method and the BrdU-SPA method is that both require BrdU incorporation, which can perturb normal cellular physiology and induce technical artifacts.

Other methods have been developed to detect and isolate stem cells using antibodies or peptides that specifically bind to cell surface marker proteins (Uchida N., et al., Proc. Natl. Acad. Sci. USA 2000, 97:14720-14725; Kiel M J, et al., Cell 2005, 121:1109-1121; Lawson, et al., Proc Natl Acad Sci USA 2007, 104:181-186; Morita T, et al. Biotechnol. Prog. 2006, 22:974-978) or based on transfection of plasmid with the promoter and reporter genes in the case of induced pluripotent stem cells (Kim J H, et al. Nature 2002, 418:50-56; Yoshizaki T, et al., Neurosci. Lett. 2004, 363:33-37). The latter transgenic detection method suffers from low sensitivity; since it can only detect cells are that effectively transfected. Won Jong Rhee and Gang Bao 2009 (BMC Biotechnology 2009, 9:30) described a method for detecting and isolating of stem cells by targeting both an intracellular marker (mRNA) and a cell surface marker (SSEA-1 protein). The Wnt target gene Lgr5 has been recently identified as a novel stem cell marker of the intestinal and colonic epithelia and the hair follicle. However, it is unclear whether Lgr5 is expressed specifically by tissue stem cells or the more abundant immediate committed progenitor cells that they produce (Snippert et al., Cell 2010, 143:134-44). This uncertainty highlights a common limitation of all described methods based simply on "TSSC marker" expression, whether endogenous or transgenic. The markers are not exclusive to TSSCs, but are also expressed by their immediate cell products, which are committed to differentiation.

SUMMARY OF THE INVENTION

Embodiments of the present invention are based on the discovery that specific proteins undergo asymmetrical cellular distribution during cell division in tissue specific stem cells (TSSC) which are also known as somatic stem cells or adult stem cells. Asymmetric cell division (also known as asymmetric cell kinetics or self renewal) continuously produces two cells whose phenotypic relationship is mother and daughter. One cell, "the mother," retains the uncommitted TSSC phenotype of its TSSC parent, whereas the other cell, "the daughter," is committed to tissue differentiation. This continuous asymmetric cell division (i.e., of the mother TSSC) is a unique feature of TSSCs. By this cellular program, individual TSSCs produce differentiating cell while simultaneously maintaining their own undifferentiated, multipotent, proliferative state, i.e., during asymmetrical cell kinetics, a TSSC will divide to give a differentiating cell and a TSSC. The inventors have found that certain nuclear proteins: CXCR-6, BTG2, LRG5 and H2A.Z, distribute primarily to the new mother TSSC during asymmetric cell kinetics of a TSSC and not to the daughter cell that can go on to produce progeny that differentiate into mature functional tissue cells. In contrast, when the TSSCs are self-renewing symmetrically, CXCR-6, BTG2, LRG5 and H2A.Z distribute evenly between the two resulting stem cells arising from the symmetrically cell division (FIG. 3-5).

CXCR-6, BTG2, and H2A.Z are products of the asymmetric self-renewal associated (ASRA) genes. These ASRA proteins exhibit unique pattern-specific distribution in a cell that undergoes asymmetric cell kinetics in contrast to a cell that undergoes symmetric cell kinetics. During TSSC asymmetric self renewal division, these ASRA proteins are located predominantly in the cycling "mother" stem cell and are not found in the differentiating non-stem cell; whereas during symmetric self-renewal division, these ASRA proteins are uniformly distributed between both daughter cells (FIG. 9). By in situ staining for the ASRA proteins CXCR-6, BTG2, LGR5 and/or H2A.Z in a cytological sample of cells, the inventors can detect and count the number of TSSC (i.e., cell that are asymmetrically self renewing), and thereby calculate the percent of TSSC in a sample of cells.

Accordingly, the present invention provides a method for determining a percent of TSSC in a sample of cells comprising: (a) contacting a sample of cells with an antibody against an ASRA protein wherein an antibody-protein complex is formed in situ; (b) detecting the antibody-protein complex; (c) counting the total number of cells in the sample and the number of cell comprising the antibody-protein complex; (d) and computing the percent of TSSC in the sample by dividing the number of cell comprising the antibody-protein complex with the total number of cells in the sample.

In one embodiment, the invention provides a method for determining a percent of TSSC in a tissue comprising: (a) obtaining a biological sample from the tissue; (b) contacting the biological sample with an antibody against an ASRA protein wherein an antibody-protein complex is formed in situ; (c) detecting the antibody-protein complex; (d) counting the total number of cells in the biological sample and the number of cells comprising the antibody-protein complex; and (e) computing the percent of TSSCs in the tissue by dividing the number of cell comprising the antibody-protein complex with the total number of cells in the biological sample.

The method of detecting, counting and determining the percent of TSSC can be applied to any situations in which the percent of TSSC is desired or in any population of cells wherein there are some cells exhibiting asymmetrical cell kinetics. The method can also be used in any population of cells wherein some cells have ASRA proteins that are expressed and cycle asymmetrically during cell division. Examples of such situations include, but are not limited to, in laboratory research on adult stem cells, in drug development tests wherein the drugs are potential modulators of TSSC expansion or differentiation, clinical trials of drugs that kill cancer stem cells, drugs that mobilizes stem cells from storage niches in the body, and drugs that stimulate expansion of stem cells, usage as a control method for the development of better TSSC isolation methods, in determining the TSSCs in clinical cell samples as a prognostic indicator and therapeutic index, as a diagnostic and prognostic indicator e.g., monitoring efficacy/toxicity of anti-cancer drugs, and in monitoring TSSC expansion, e.g., in cell manufacturing processes. In other embodiments, the method can be used for any population of cells from reprogrammed, induced pluripotent stem cells or even embryonic stem cells that have undergone some degree of differentiation to a multipotent cell instead of a pluripotent cell in the beginning.

In another embodiment, the invention provides a method of monitoring an expansion of TSSCs, the method comprising: (a) obtaining a biological sample containing TSSC at least two time points, a first and a second time point; (b) contacting an aliqout of TSSC obtained at least two time point with an antibody against an ASRA protein wherein an antibody-protein complex is formed in situ; (c) detecting the antibody-protein complex; (d) counting the total number of cells and the number of cells comprising the antibody-protein complex in each aliqout; (e) computing the percent of TSSC in each aliqout by dividing the number of cells comprising the antibody-protein complex with the total number of cells in the aliqout of the respective time point, wherein if the percent of TSSC is greater in the second time point compared to the first time point indicates that the number of TSSCs is expanding.

In one embodiment, the invention provides a method of determining efficacy of a drug on a culture of TSSCs ex vivo, the method comprising: (a) culturing, in parallel, a population of TSSC in the presence of a drug and a population of TSSC in the absence of the drug; (b) obtaining a sample of TSSC from each of the populations; (c) contacting the samples of TSSC with an antibody against an ASRA protein wherein an antibody-protein complex is formed in situ; (d) detecting the antibody-protein complex; (e) counting the total number of cells and the number of cells comprising the antibody-protein complex in each sample; (f) computing the percent of TSSC in each sample by dividing the number of cells comprising the antibody-protein complex with the total number of cells in the respective sample, wherein if the percent of TSSC in the sample in the presence of the drug is greater than the percent of TSSC in the sample in the absence of the drug indicates that the culture is expanding and the drug is a positive modulator of TSSC, wherein if the number of TSSC in the sample in the presence of the drug is less than the percent of TSSC in the sample in the absence of the drug indicates that the culture is decreasing and the drug is a negative modulator of TSSC; and wherein if the percent of TSSC in the sample in the presence of the drug is about equal to the percent of TSSC in a sample in the absence of the drug indicates that the drug has no effect on the growth and expansion of the TSSCs.

In one embodiment, the invention provides a method of determining efficacy of a drug on TSSC in vivo, the method comprising: (a) administering the drug to a subject; (b) contacting a sample of TSSC from the subject with an antibody against an ASRA protein wherein an antibody-protein complex is formed in situ; (c) detecting the antibody-protein complex; (d) counting the total number of cells and the number of cells comprising the antibody-protein complex in the sample; (e) computing the percent of TSSC in the sample by dividing the number of cells comprising the antibody-protein complex with the total number of cells in the respective sample, wherein if the percent of TSSC is greater than a control indicates that the number of TSSC is expanding in vivo and the drug is a positive modulator of TSSC, wherein if the percent of TSSC is less than the control indicates that the number of TSSC is vivo is decreasing and the drug is a negative modulator of TSSC and wherein if the percent of TSSC is about the equal with the control indicates that the drug has no effect on the expansion of TSSCs in vivo.

In another embodiment, the invention provides a method of prognosing a therapeutic efficacy of a population of TSSCs for transplantation, the method comprising: (a) contacting an aliquot sample of cells from the population of TSSC with an antibody against an ASRA protein wherein an antibody-protein complex is formed in situ; (b) detecting the antibody-protein complex; (c) counting the total number of cells and the number of cells comprising the antibody-protein complex in the sample; and (d) computing the percent of TSSC in the sample by dividing the number of cells comprising the anti-body-protein complex with the total number of cells in the respective sample, wherein the percent of TSSC is greater than a control indicates that the population of TSSCs will likely be therapeutically effective. For example, in the context of transplantation of hematopoietic stem cells, liver stem cells, pancreas or neural stem cells etc, this method can be used to determine if there is the minimum number of stem cells in the population of cells to be transplanted into a patient such that there is about at least 70% chance of a success, i.e., sufficient transplanted stem cells will establish residence in the recipient and produce functional differentiated cells to replace the recipient's defective cells. For bone marrow transplant, the minimum number of CD34+ hematopoietic stem cells is about 1-2 million.

In addition, the inventors also found that using known cell cycle-specific proteins (CCSPs), such as cyclin A, cyclin D1, and cyclin E, in the described cytological staining methods, it is possible to detect asymmetrical self-renewing TSSCs (see FIG. 1-7). Accordingly, in some embodiments, CCSPs can be used to detect, count the number of TSSC in the sample and thereby calculate the percent of TSSC in a sample of cells.

In some embodiments of the methods, the method further comprises detecting cells with pattern-specific asymmetric localization of the antibody-protein complex; counting the total number of cells in the sample, a population of cells or a sample of tissue and the number of cell comprising the asymmetrically localized antibody-protein complex; and computing the percent of TSSC in the sample by dividing the number of cell comprising the asymmetrically localized antibody-protein complex with the total number of cells in the sample, a population of cells or a sample of tissue.

In one embodiment of any methods described herein, a CCSP is used instead of an ASRA protein. In another embodiment of any methods described herein, a CCSP is used in addition to an ASRA protein.

In some embodiments, the ASRA protein or the CCSP is a pattern-specific asymmetrically located protein in a cell undergoing asymmetrical cell kinetics.

In one embodiment, only the number of cells comprising pattern-specific asymmetrically located antibody-protein complex are counted and used in the computation of the percent TSSCs.

In one embodiment, the ASRA protein is selected from a group consisting of CXCR-6, BTG2, LGR5, or H2A.Z. In other embodiments, the ASRA protein is selected from the proteins encoded by the genes disclosed in U.S. Patent Application 2009/0142760, wherein the genes expressions are altered in cells exhibiting asymmetric self-renewal relative to symmetric self-renewal division.

In one embodiment, the CCSP is selected from the group consisting of cyclin A, cyclin D1, cyclin E, cyclin dependent kinase inhibitor 1A (CDKN1A; also known as p21waf1), thymidine kinase (TK), Ki67, thymidylate synthase (TS), dihydrofolate reductase (DHFR) and the GAS-X proteins (growth arrest-specific proteins 1, 2, 3 etc).

In one embodiment of any methods described herein, a combination of a CCSP and an ASRA protein is used.

In one embodiment, the sample of cells is grown and cultured in low cell density of about $1 \times 10^3$ cells/ml. In one embodiment, the sample of cells is grown and cultured in low cell density of about ≥500 cells/cm$^2$.

In one embodiment, the sample of cells are grown and cultured in high cell density of about $1 \times 10^5$ cells/ml to about $5 \times 10^6$ cells/ml. In one embodiment, the sample of cells is grown and cultured in high cell density of about >500 cells/cm$^2$, up to 10,000 cells/cm$^2$.

In one embodiment, the sample of cells is fixed and permeabilized prior contacting with the antibody against an ASRA.

In one embodiment, the TSSC is expanded in vivo.
In one embodiment, the TSSC is expanded ex vivo.
In one embodiment, the TSSC is expanded in culture.
In one embodiment, the control is the percent of TSSC in a sample from the subject prior to administration of the drug or at an earlier time point, wherein the number of TSSCs in the sample is determined by the same method as used for computing the percent of TSSC after administration of drug.

In one embodiment, the control is the percent of TSSC in a population of TSSCs that when transplanted into a patient there is about at least 70% chance of a transplantation success, i.e., sufficient transplanted stem cells will establish residence in the recipient and produce functional differentiated cells to replace the recipient's defective cells.

In one embodiment, the TSSC is a hematopoietic stem cell or a hair follicle stem cell.

In one embodiment, the TSSC is a hematopoietic stem cell, is expanded and the transplantation is bone marrow transplantation. In another embodiment, the TSSC is a hair follicle stem cell for used in hair replacement therapy.

In one embodiment, the TSSC is obtained from a source selected from a group consisting of cord blood, bone marrow and mobilized peripheral blood.

DETAILED DESCRIPTION OF THE INVENTION

Figure 1:
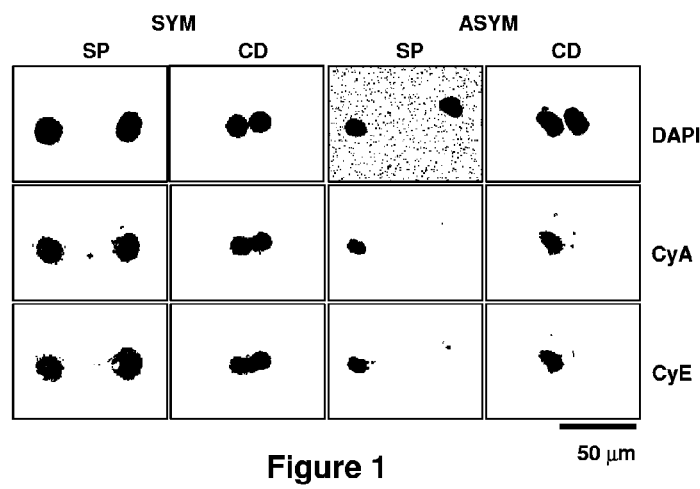
FIG. 1 shows the initial demonstration of CCSP-SPA (SP) and CCSP-Cyto D (CD) assays using engineered cell lines that undergo TSSC symmetric (SYM) or asymmetric self-renewal (ASYM) under experimental control. The inverted fluorescence images are shown. Cyclin A and cyclin E are cell cycle specific proteins (CCSPs).

Embodiments of the present invention are based on the discovery that specific proteins undergo asymmetrical cellular distribution during cell division in tissue specific stem cells (TSSC) which are also known as somatic stem cells and adult stem cells. Asymmetric self-renewal (or cell kinetics) continuously produces two cells whose phenotypic relationship is mother and daughter. One cell, "the mother," retains the uncommitted TSSC phenotype of its TSSC parent, whereas the other cell, "the daughter," is committed to tissue differentiation. This continuous asymmetric self-renewal (i.e., of the mother TSSC) is a unique feature of TSSCs. By this cellular program, individual TSSCs produce differentiating cells while simultaneously maintaining their own undifferentiated, multipotent, proliferative state. The inventors have found that certain predominantly nuclear proteins: BTG2, LGR5 and H2A.Z, distribute primarily to the new TSSC during asymmetric cell kinetics and not to the daughter cell that produces progeny that differentiate into mature, functional tissue cells. In contrast, when the TSSCs are self-renewing symmetrically, BTG2, LRG5 and H2A.Z distribute evenly between the two resulting stem cells arising from the symmetric cell division. For CXCR-6, which shows a both nuclear and cytoplasmic expression there is lower or no expression in the nuclei of symmetrically cycling cells compared to the resulting mother cell of an asymmetrical cell kinetics. Moreover, CXCR-6 expression is greatly increased during asymmetric cell kinetics and this increased CXCR-6 expression is predominately located in the nucleus of the resulting mother cell. This unique distribution of ARSA protein detection in asymmetrically cycling cells is known as pattern-specific asymmetric localization. CXCR-6, BTG2 and/or H2A.Z are gene products of some of the genes whose expression levels differ between the asymmetric self-renewal state and the symmetric self-renewal state of TSSCs described in U.S. Patent Application No. 2009/0142760.

CXCR-6, BTG2 and H2A.Z are products of the asymmetric self-renewal associated (ASRA) genes. By in situ staining for CXCR-6, BTG2, LGR5 and/or H2A.Z in a cytological sample of cells, the inventors can detect TSSCs, count the number of TSSC in the sample, and thereby calculate the percent of TSSC in the sample of cells.

In addition, the inventors also demonstrated that using known cell cycle-specific proteins (CCSPs), such as cyclin A, cyclin D1, and cyclin E, in the described cytological staining methods, it is possible to detect asymmetrical self-renewing TSSCs (see FIG. 1-7). CCSPs are well known in the art (see Morgan D O, 2007, "The Cell Cycle: Principles of Control", New Science Press, Ltd; and Nigg E A, 1995, Bioessays 17: 471-80). Accordingly, in some embodiments, CCSPs can be used to detect, count the number of TSSC in the sample and thereby calculate the percent of TSSC in a sample of cells.

Accordingly, in one embodiment, the present invention provides a method for determining a percent of TSSC in a sample of cells comprising: (a) contacting a sample of cells with an antibody against an ASRA protein wherein an antibody-protein complex is formed in situ; (b) detecting the antibody-protein complex; (c) counting the total number of cells in the sample and the number of cell comprising the antibody-protein complex; and (d) computing the percent of TSSC in the sample by dividing the number of cell comprising the antibody-protein complex with the total number of cells in the sample.

In one embodiment, the present invention provides a method for determining a percent of TSSC in a sample of cells comprising: (a) contacting a sample of cells with an antibody against an ASRA protein wherein an antibody-protein complex is formed in situ; (b) detecting the antibody-protein complex; (c) counting the total number of cells in the sample and the number of cell comprising the pattern-specific asymmetrically localized antibody-protein complex; and (d) computing the percent of TSSC in the sample by dividing the number of cell comprising the asymmetrically localized antibody-protein complex with the total number of cells in the sample.

In one embodiment of any methods described herein, a CCSP is used instead of an ASRA protein.

Accordingly, in another embodiment, the present invention provides a method for determining a percent of TSSC in a sample of cells comprising: (a) contacting a sample of cells with an antibody against a CCSP wherein an antibody-protein complex is formed in situ; (b) detecting the antibody-protein complex; (c) counting the total number of cells in the sample and the number of cell comprising the antibody-protein complex; and (d) computing the percent of TSSC in the sample by dividing the number of cell comprising the antibody-protein complex with the total number of cells in the sample.

In another embodiment, the present invention provides a method for determining a percent of TSSC in a sample of cells comprising: (a) contacting a sample of cells with an antibody against a CCSP wherein an antibody-protein complex is formed in situ; (b) detecting the antibody-protein complex; (c) counting the total number of cells in the sample and the number of cell comprising the pattern-specific asymmetrically localized antibody-protein complex; and (d) computing the percent of TSSC in the sample by dividing the number of cell comprising the asymmetrically localized antibody-protein complex with the total number of cells in the sample.

In one embodiment, when CCSPs are used in the methods described, the cytokinesis phase of a cell cycle is prevented or inhibited, for example, by cytochalasin D.

In one embodiment of any methods described herein, a combination of at least one ASRA protein and at least one CCSP is selected for analysis, for example, LGR5 and cyclin A. In this example, a first antibody against the selected CCSP and a second antibody against the selected ASRA protein are used to contact the sample of cells, a biological sample comprising TSSP or a sample of tissue.

In one embodiment, the sample of cells is a suspension of cells in an aqueous medium, e.g., a cell culture media. In some embodiments, the suspension of cells can comprised of dissociated cells from a sample of tissue or the tissue itself, e.g., a sample of peripheral blood or bone marrow. The medium should be an isotonic medium to the cell cytoplasm such that the cells do not undergo cell lysis in the medium and they remain viable cells capable of undergoing at least one cell division, e.g., phosphate buffered saline (PBS). Cell culture media, PBS and similar media for suspending but not cause cell lysis are well known in the art.

In one embodiment, the sample of cells comprises cells cultured on a solid support wherein the cells have adhered to the solid support, e.g., in a tissue culture dish, a glass coverslip or a glass slide. Methods of culturing cells on solid supports are also well known to one skilled in the art.

In one embodiment, the sample of cells is a tissue. In one embodiment, the tissue is a solid mass of cells, much like a tissue biopsy from an organ or body part. The solid mass of cells can be cut to small pieces and digested with enzyme to break down the connective matrix that hold the cells together in the solid tissue. The digested material can then be filtered to obtain single dissociated cells. These single viable cells are then used or grown in culture on a solid support or in suspension. In another embodiment, the sample of cells is a tissue section from a tissue. Methods of preparing dissociated cells from solid tissues and preparing tissue sections from a tissue for immunohistochemical staining are well known to a skilled artisan of the art.

In one embodiment, the tissue is a suspension of cells, e.g., whole blood and bone marrow.

Accordingly, in one embodiment, the present invention provides a method for determining a percent of TSSC in a tissue comprising: (a) obtaining a biological sample from the tissue; (b) contacting the biological sample with an antibody against an ASRA protein and/or a CCSP wherein an antibody-protein complex is formed in situ; (c) detecting the antibody-protein complex; (d) counting the total number of cells in the biological sample and the number of cells comprising the antibody-protein complex; and (e) computing the percent of TSSC in the tissue by dividing the number of cell comprising the antibody-protein complex with the total number of cells in the biological sample.

In one embodiment, the biological sample from the tissue comprises a sample of cells, wherein the sample of cells is a suspension of cells dissociated from the tissue or a tissue comprising a suspension of cells, e.g., whole blood and bone marrow.

In one embodiment, the method involves fixing the sample of cells, permeabilizing the cell membrane and nuclear membranes of the cells to allow the specific anti-CXCR-6, anti-BTG2, anti-LGR5, anti-H2A.Z antibodies or anti-CCSP antibodies to enter the fixed cells. This facilitates the antibody binding their respective antigen proteins in the nucleus of the TSSC. Methods of preparing cells of cytological analysis are well known to one skilled in the art, for example, fixatives include but are not limited to glutaldehyde and paraformaldehyde; permeabilization agents include TRITON X-100® and TWEEN-20.

In one embodiment, the ASRA protein is selected from a group consisting of CXCR-6, BTG2, LGR5, LRG6 or H2A.Z.

Chemokine (C-X-C motif) receptor 6 (CXCR-6) (GeneID: 10663) or G protein-coupled receptor TYMSTR is also known as BONZO, CD186, STRL33 and TYMSTR. It is localized to the cell membrane and the nucleus. It is involved in cytokine-cytokine receptor interaction and in the chemokine signaling pathway. Anti-CXCR-6 antibodies are commercially available, e.g., from ABCAM® catalog #ab8822, #ab8023 and #ab76084.

B-cell translocation gene 2 (GeneID: 7832), BTG family, member 2, is also known as PC3, TIS21, MGC126063, MGC126064 and BTG2. Other names include pheochromacytoma cell-3, NGF-inducible anti-proliferative protein PC3 and nerve growth factor-inducible anti-proliferative factor. The protein is a member of the BTG/Tob family. This family has structurally related proteins that appear to have anti-proliferative properties. BTG2 is involved in the regulation of the G1/S transition of the cell cycle. Anti-BTG2 antibodies are commercially available, e.g., from ABCAM® catalog #ab58219 and #ab85051.

H2A histone family, member Z (GeneID: 3015) is also known as H2AZ, H2A.z, H2A/z, H2A.Z, MGC117173 and H2AFZ. Other names include H2AZ histone. Histones are basic nuclear proteins that are responsible for the nucleosome structure of the chromosomal fiber in eukaryotes. Nucleosomes consist of approximately 146 bp of DNA wrapped around a histone octamer composed of pairs of each of the four core histones (H2A, $H_2B$, H3, and H4). The chromatin fiber is further compacted through the interaction of a linker histone, H1, with the DNA between the nucleosomes to form higher order chromatin structures. H2AZ is a replication-independent member of the histone H2A family that is distinct from other members of the family. Studies in mice have shown that this particular histone is required for embryonic development and indicate that lack of functional histone H2A leads to embryonic lethality. Anti-H2A.Z antibodies are commercially available, e.g., from ABCAM® catalog #ab4174 and #ab4626.

In one embodiment, the CCSP is selected from the group consisting of cyclin A, cyclin D1, cyclin E, CDKN1A, TK, Ki67, TS, DHFR and the GAS-X proteins (growth arrest-specific proteins 1, 2, 3 etc).

In one embodiment, the sample of cells is allowed to divide at least once. In one embodiment, the sample of cells is fixed and permeabilized prior contacting with the antibody against an ASRA protein and/or a CCSP, specifically contacting with an anti-CXCR-6, anti-BTG2, anti-LGR5, anti-H2A.Z antibody, anti-CCSP antibody (e.g., anti-cyA, anti-cyD1 and anti-CDKN1A). The antibody binds its respective antigen and forms an antibody-protein complex. This complex is detected by way of the antibody in the complex. In one embodiment, the antibody-protein complex is detectably label. For example, the antibodies against CXCR-6, BTG2, LGR5 and H2A.Z are directly labeled with a tag such as a fluorescent dye or a radioactive isotope. Methods of directly labeling antibodies are known to one skilled in the art. Alternatively, the antibodies against CXCR-6, BTG2, LGR5 and H2A.Z are detected by a labeled secondary antibody that specifically bind the antibodies against CXCR-6, BTG2, LGR5 and H2A.FZ or the species type of the antibodies against CXCR-6, BTG2, LGR5 and H2A.Z, e.g., the antibody against BTG2 is made from a goat, the labeled secondary antibody will then be an anti-goat antibody.

In one embodiment, the sample of cells is grown and cultured in low cell density of about $1\times10^3$ cells/ml. In one embodiment, the sample of cells is grown and cultured in low cell density of about <500 cells/cm$^2$. At low cell density, after the adherent cells are allowed to undergo at least one cell division, the two sister cells arising from a single original cell can be found close together. This facilitates visual determination of both two sister cells derived from a single original cell, wherein only one of the cells (i.e., the "mother" TSSC) has the ASRA protein which indicates asymmetric self-renewal by the single original cell.

In one embodiment, the sample of cells are grown and cultured in high cell density of about $1\times10^5$ cells/ml. In one embodiment, the sample of cells is grown and cultured in high cell density of about >500 cells/cm$^2$, up to 10,000 cells/cm$^2$. At high cell density, after the cells are allowed to undergo one nuclear division and before cytokinesis, the cells are treated with cytochalasin D to block cytokinesis by inhibiting actin polymerization. This results in a binucleated cell. This facilitates visual determination and distinguishing of binucleated cells with only one nucleus that has the ASRA protein which indicates asymmetric self-renewal by the single original cell before cell division.

In one embodiment, the cells are treated with cytochalasin D to arrest cytokinesis after nuclear division. Methods of such are well known in the art, e.g., in G. W. Zieve, 1984, Am. J. Physiol. Cell. Physiol. 246: C154-C156; and Merok J R, et al., 2002, Cancer Res. 62:6791-5.

Tissue specific stem cells (TSSCs), aka somatic stem cells or adult stem cells are multipotent or unipotent. TSSCs of the present invention include any stem cells found in post-embryonic, fetal and post-natal tissues and adult tissues. TSSCs include but are not limited to bone marrow derived stem cells, adipose derived stem cells, mesenchymal stem cells, neural stem cells, liver stem cells, and pancreatic stem cells. Bone marrow derived stem cells refer to all stem cells derived from bone marrow; these include but are not limited to mesenchymal stem cells, bone marrow stromal cells, and hematopoietic stem cells. Bone marrow-derived stem cells are also known as mesenchymal stem cells or bone marrow stromal stem cells, or simply stromal cells or stem cells. These somatic stem cells can be isolated by any methods known in the art, e.g., as taught in U.S. Pat. Nos. 6,878,542, 6,436,704, 6,927,061, 6,911,533, 7,052,907, 7,560,280, 7,592,174, U.S. Patent Publication No. 2009/0238803 and International Patent Application No. WO/2003/016916. In one embodiment, the somatic stem cells are in solid tissues. TSSCs exhibit asymmetric cell kinetics as described in Rambhatla et al., J Biomed Biotechnol. 2001, 1:28-37; Sherley J L., Stem Cells, 2002, 20:561-72; Lee et al. 2003, Biotechnol. Bioeng. 83:760-71; and Pare and Sherley, 2006, Curr. Topics Developmental Biol. 73:141-71.

The method of detecting, counting and determining the percent of TSSC can be applied to any situations in which the percent of TSSC is desired. Examples of such situations include but are not limited to laboratory research on adult stem cells, in drug development tests wherein the drugs are potential modulators of TSSC expansion, differentiation or mobilization, as a control method for the development of better TSSC isolation methods, in determining the TSSCs in clinical cell samples as a prognostic indicator and therapeutic index, as a diagnostic and prognostic indicator (e.g., monitoring efficacy/toxicity of anti-cancer drugs) and in monitoring TSSC expansion, e.g., in cell manufacturing processes.

Accordingly, in one embodiment, the invention provides a method of monitoring an expansion of TSSC, the method comprising: (a) obtaining a biological sample containing TSSC at least two time points, a first and a second time point, wherein the second time point is after the first time point; (b) contacting an aliquot of TSSC obtained at least two time point with an antibody against an ASRA protein and/or a CCSP wherein an antibody-protein complex is formed in situ; (c)

detecting the antibody-protein complex; (d) counting the total number of cells and the number of cells comprising the antibody-protein complex in each aliquot; and (e) computing the percent of TSSC in each aliqout by dividing the number of cells comprising the antibody-protein complex with the total number of cells in the aliqout of the respective time point, wherein if the percent of TSSC is greater in the second time point compared to the first time point indicates that the TSSC is expanding.

In one embodiment, the TSSC is expanded ex vivo, i.e., outside a living organism. For example, the TSSC is hematopoietic stem cell (HSC) that is harvested for bone marrow transplantation. The method can be used to initially determine the percent of HSC and then used to compute the total number of HSC in the harvest. If the total number of HSC is below the number that is considered necessary for the transplant to have a reasonable success, then the initial harvest of HSC can be expanded ex vivo with biological factors that have been shown to stimulate ex vivo expansion of HSCs, for example, angiopoietin-like 5, IGFBP2, insulin-like growth factor-binding protein 2, and prostaglandin D2, and aryl hydrocarbon receptor antagonists (Zhang C C. et al., Nat. Med. 2006, 12:240-5; Zhang C C. et al., Blood, 2008, 111:3415-23; Huynh H. et al., Stem Cells, 2008, 26:1628-35; North T E. et al., Nature, 2007, 447:1007-11; Boitano et al., Science, 2010, 329:1345-8). During the expansion phase, periodic sampling of the expansion culture can be obtained and the number or percent of HSC in the samples can be determined using the method described herein. It is contemplated that the number or percent of HSC would be increasing at each later time point of sampling with respect to the number or percent of HSC obtained at an earlier time, e.g., the immediate previous time point. When the number or percent of HSC from the most recent sample, i.e., later time point, indicates that the target number of HSC necessary for successful transplantation have been reached in the ex vivo expansion phase, the HSC can be harvested and then implanted into the recipient.

In one embodiment, the TSSC is expanded in culture, i.e., cells are kept in containers. For example, hematopoietic, mesenchymal, and neural stem cells can be expanded in culture for a variety of uses, e.g., therapeutic, tissue engineering and research purposes. During the expansion in culture, periodic sampling of the expansion culture can be obtained and the number or percent of HSC can be determined using the method. When the number or percent of HSC from the most recent sample indicates that the target number of HSC has been reached in the expansion process, the HSC is then harvested and used. Methods of expanding stem cells in vitro are well known in the art, e.g., in U.S. Pat. Nos. 5,728,581; 5,908,784 and U.S. Patent Application No. 2004/0018620; 2005/072147; and 2009/0148420.

In one embodiment, the invention provides a method of monitoring an increase in the TSSC fraction in a peripheral blood in a donor individual until it reaches a critical level for collection, the method comprising: (a) obtaining a biological peripheral blood sample containing TSSC at least two time points, a first and a second time point, wherein the second time point is after the first time point; (b) contacting an aliquot of TSSC obtained at least two time point with an antibody against an ASRA protein and/or a CCSP wherein an antibody-protein complex is formed in situ; (c) detecting the antibody-protein complex; (d) counting the total number of cells and the number of cells comprising the antibody-protein complex in each aliquot; (e) computing the percent of TSSC in each aliquot by dividing the number of cells comprising the antibody-protein complex with the total number of cells in the aliquot of the respective time point, wherein if the percent of TSSC is greater in the second time point compared to the first time point indicates that the TSSC has increased since the first time point. In one embodiment, the donor individual is a mammal, preferably a primate mammal, and more preferably, a human.

In one embodiment, the TSSC in a HSC and the HSC is mobilized in vivo, i.e., inside a living organism. For example, growth factors GM-CSF and G-CSF can be administered to a potential donor of HSC to mobilize the existing HSC in the bone marrow niches to the peripheral circulating blood in vivo in order to increase the fraction of HSCs circulating in the blood. Periodic sampling of the circulating blood from the donor is obtained and the number or percent of HSC is determined using the method. When the number or percent of HSC from the most recent sample indicates that the target number of HSC necessary for successful transplantation have been reached in the peripheral blood, the HSC can be harvested from the donor and then implanted into the recipient needing the HSC.

Accordingly, in one embodiment, the invention also provides a method of prognosing a therapeutic efficacy of a population of TSSC for implantation, the method comprising: (a) contacting an aliqout sample of cells from the population of TSSC with an antibody against an ASRA protein and/or a CCSP wherein an antibody-protein complex is formed in situ; (b) detecting the antibody-protein complex; (c) counting the total number of cells and the number of cells comprising the antibody-protein complex in the sample; (d) computing the percent of TSSC in the sample by dividing the number of cells comprising the antibody-protein complex with the total number of cells in the respective sample, wherein the percent of TSSC is greater than a control indicates that the population of TSSC will likely be therapeutically effective. In some embodiments such as in the context of transplantation of HSCs, liver stem cells, pancreas or neural stem cells etc, this method can be used to determine if there is the minimum number of stem cells in the population of cells or sample of cells to be transplanted into a patient such that there is about at least 70% chance of a success.

In one embodiment, the control is the percent of TSSC in a population of TSSC that when transplanted into a patient there is about at least 70% chance of a transplantation success, i.e., sufficient transplanted stem cells will establish residence in the recipient and produce functional differentiated cells to replace the recipient's defective cells. For bone marrow transplant, the minimum number of CD34+ HSC is about 1-2 million.

In one embodiment, the method is applied to HSCs for use in transplantation therapy. From a larger known quantity of HSCs that is isolated from a donor, a small sample of known quantity is taken to determine the number of stem cells by the method. The amount of stem cells obtained for the small sample is used to estimate the number of stem cells in the larger quantity to determine whether there is sufficient number of HSCs for transplantation therapy.

In one embodiment, the method comprises obtaining a population of TSSC for transplantation. Such population can be obtained from a donor individual, e.g., from a human, from frozen umbilical cord blood or from mouse embryonic stem cells that have been differentiated. In one embodiment, the TSSC is HSCs and the population of TSSC is selected from a group consisting of cord blood, bone marrow and mobilized peripheral blood.

In one embodiment, the TSSC is a HSC and the implantation is for bone marrow transplantation, umbilical cord blood or peripheral blood transplantation. In one embodiment, the HSC is expanded in vivo or ex vivo.

In one embodiment, the TSSC is a neural stem cell. Therapeutic implantation of neural stem cells can be for but not limited to any neurodegenerative diseases, e.g., Parkinson's disease, any form of neuropathy, or spinal cord injury. In one embodiment, the neural stem cell is expanded in vivo or ex vivo.

In one embodiment, the TSSC is a adipose stem cell. Implantation of adipose stem cells can be for but not limited to cosmetic/plastic surgery, tissue engineering and reconstruction surgery. In one embodiment, the adipose stem cell is expanded in vivo or ex vivo.

In one embodiment, the TSSC is hair follicle stem cell. The counting in for the number of hair follicle stem cells available for use in hair transplant preparations. In one embodiment, the hair follicle stem cell is expanded in vivo or ex vivo.

In one embodiment, the TSSC is a pancreatic stem cell, wherein the pancreatic stem cells are used in transplantation into the pancreas for the treatment of diabetes. In one embodiment, the pancreatic stem cell is expanded in vivo or ex vivo.

In one embodiment, the TSSC is a hepatic stem cell, wherein the hepatic stem cells are used in transplantation into the liver for the treatment of liver failure. In one embodiment, the hepatic stem cell is expanded in vivo or ex vivo.

In another embodiment, the TSSC is a kidney stem cell, wherein the adrenal stem cells are used in transplantation into the liver for the treatment of kidney failure. In one embodiment, the kidney stem cell is expanded in vivo or ex vivo.

In some embodiments, the method can be used during the development of drugs and/or screening of compound/agent that can modulate TSSC. For example, drugs, compounds or agents that promote expansion of TSSC in vivo, ex vivo, or in culture; drugs, compounds or agents that promote differentiation of TSSC in vivo, ex vivo, or in culture; drugs, compounds or agents that promote the mobilization of TSSC from storage niches in vivo; and drugs, compounds or agents that "kills" cancer stem cells in vivo, ex vivo, or in culture. As used herein, the term "kill" means inhibit cell growth and cell division, or promote cell death by (by apoptosis, autophagy, or necrosis) or cellular senescence.

Accordingly, in one embodiment, the invention provides a method of determining efficacy of a drug on an ex vivo culture of TSSC, the method comprising: (a) culturing, in parallel, a population of TSSC in the presence of a drug and a population of TSSC in the absence of the drug; (b) obtaining a sample of TSSC from each of the populations; (c) contacting the samples of TSSC with an antibody against an ASRA protein and/or a CCSP wherein an antibody-protein complex is formed in situ; (d) detecting the antibody-protein complex; (e) counting the total number of cells and the number of cells comprising the antibody-protein complex in each sample; (f) computing the percent of TSSC in each sample by dividing the number of cells comprising the antibody-protein complex with the total number of cells in the respective sample, wherein if the percent of TSSC in the sample in the presence of the drug is greater than the percent of TSSC in the sample in the absence of the drug indicates that the culture is expanding and the drug is a positive modulator of TSSC, wherein if the number of TSSC in the sample in the presence of the drug is less than the percent of TSSC in the sample in the absence of the drug indicates that the culture is decreasing and the drug is a negative modulator of TSSC; and wherein if the percent of TSSC in the sample in the presence of the drug is about equal to the percent of TSSC in a sample in the absence of the drug indicates that the drug has no effect on the growth and expansion of the TSSC in culture.

In another embodiment, the invention provides a method of determining efficacy of a drug on TSSC in vivo, the method comprising: (a) administering the drug to a subject; (b) obtaining a tissue sample comprising TSSC from the subject; (c) contacting the sample of TSSC from the subject with an antibody against an ASRA protein and/or a CCSP wherein an antibody-protein complex is formed in situ; (d) detecting the antibody-protein complex; (e) counting the total number of cells and the number of cells comprising the antibody-protein complex in the sample; and (f) computing the percent of TSSC in the sample by dividing the number of cells comprising the antibody-protein complex with the total number of cells in the respective sample, wherein if the percent of TSSC is greater than a control indicate that the TSSC is expanding in vivo and the drug is a positive modulator of TSSC, wherein if the percent of TSSC is less than a control indicate that the TSSC is expanding and the drug is a negative modulator of TSSC, and wherein if the percent of TSSC is about the equal with the control indicate that the drug has no effect on the expansion of TSSC in vivo.

In one embodiment, the control is the percent of TSSCs in a sample from the subject prior to administration of the drug or at an earlier time point, wherein the number of TSSC in the sample is determined by the same method as used for computing the percent of TSSC after administration of drug.

The percent of TSSCs is greater than a control by at least 10%, at least 20%, at least 30%, at least 40%, at least 50%, at least 60%, at least 70%, at least 80%, at least 90%, at least 100% or more, including all the intervening percentages between 10% and 100%.

The percent of TSSCs is less than a control by at least 5%, at least 10%, at least 20%, at least 30%, at least 40%, at least 50%, at least 60%, at least 70%, at least 80%, at least 90%, at least 100% or more, including all the intervening percentages between 10% and 100%.

As used herein, the term "efficacy" of a drug on TSSC refers to the drug's ability to promote expansion, promote differentiation or "kills", i.e., promotes cell death, cell cycle arrest, or senescence is a TSSC.

TSSCs can undergo symmetric or asymmetric cell kinetics depending on various conditions and external factors. CCSPs cannot be used to distinguish symmetrically cycling stem cells because transient-amplifying cells would give a symmetric expression pattern with CCSPs. However, CCSPs can be used with cytochalasin D to distinguish asymmetrically cycling TSSCs from transient-amplifying cells that do not undergo asymmetric self-renewal. The ASRA protein H2A.Z is similar to CCSPs in this respect (Huh et al., submitted). BTG2 and LGR5 have yet to be evaluated directly in transiently amplifying cells, however, nuclear CXCR-6, differs because not only does it show pattern-specific localization to the asymmetrically self-renewing TSSC, but it is also detected at significantly lower levels in the nuclei of symmetrically self-renewing cells (data not shown). CXCR-6 exhibited a lower or no expression in symmetrically cycling cells compared to the mother cell of asymmetric cell divisions. In asymmetrically cycling cells, nuclear CXCR6 expression is higher in the nuclei of these cells compared to symmetrically cycling cells. In contrast, H2A.Z, BTG2, and LGR5 show similar levels of expression in all cycling cells, whether asymmetric or symmetric.

Adult somatic stem cells, including liver stem cells, predominantly divide by asymmetric cell kinetics. While somatic stem cells also undergo limited symmetric divisions (that produce two identical stem cells) in developing adult tissues, such symmetric kinetics is restricted to periods of tissue expansion and tissue repair. Inappropriate symmetric tissue stem cell divisions evoke mechanisms leading to apoptosis of duplicitous stem cells (Potten and Grant, 1998, Br. J.

Cancer, 78:993-1003). Some stem cells may also lie dormant for long periods before initiating division in response to specific developmental cues, as in reproductive tissues like the breast. However, the predominant cell kinetics state of tissue stem cells is asymmetric.

During asymmetric cell kinetics, one daughter cell divides with the same kinetics as its stem cell parent, while the second daughter gives rise to a differentiating non-dividing cell lineage. The second daughter may differentiate immediately; or depending on the tissue, it may undergo a finite number of successive symmetric divisions to give rise to a larger pool of differentiating cells. The second daughter and its dividing progeny are called transiently amplifying cells or transit cells. Transit cell divisions ultimately result in mature, differentiated, terminally arrested cells. In tissues with high rates of cell turnover, the endpoint for differentiated terminal cells is programmed cell death by apoptosis.

Asymmetric cell kinetics evolved in vertebrates as a mechanism to insure tissue cell renewal while maintaining a limited set of stem cells and constant adult body mass. Mutations that disrupt asymmetric cell kinetics are an absolute requirement for the formation of a clinically significant tumor mass. In many ways, asymmetric cell kinetics provides a critical protective mechanism against the emergence of neoplastic growths that is life threatening.

In one embodiment, the present invention provides a method for detecting TSSC having asymmetrically cell kinetics in a sample of cells comprising: (a) contacting a sample of cells with an antibody against an ASRA protein and/or a CCSP wherein an antibody-protein complex is formed in situ; (b) detecting the antibody-protein complex; (c) counting the total number of cells in the sample and the number of cell comprising the antibody-protein complex; and (d) computing the percent of TSSC in the sample by dividing the number of cell comprising the antibody-protein complex with the total number of cells in the sample, wherein when the percent of TSSC is greater than a reference indicates that the sample of cells is undergoing asymmetrical cell kinetics and wherein when the percent of TSSC is greater than a reference indicate that the sample of cells is undergoing symmetrical cell kinetics. In one embodiment, a reference is the normal average TSSC fraction in a tissue, which can range from 0.001% to 1% depending on the type of tissue.

In one embodiment, the sample of cells is a tissue. In one embodiment, the sample of cells is an aliquot from a population of cells. In one embodiment, the population of cells is a mixture of asymmetrically cycling TSSCs and transiently dividing non-TSSC cells. The term "transiently dividing" and "transiently amplifying" are used interchangeably and they refer to short term cell division cycles of a cell, usually less than ten consecutive divisions.

In some embodiments, the CCSP is but not limited to cyclin A, cyclin E, and cyclin D1, cyclin-dependent kinase inhibitor 1A (aka p21, Cip1, CDKN1A), thymidine kinase (TK), antigen identified by monoclonal antibody Ki-67 (Ki67), thymidylate synthase (TS), dihydrofolate reductase (DHFR), and the growth arrest specific (GAS-X) proteins.

In some embodiments, the method enables the distinguishing the self-renewal pattern state of TSSCs, whether the TSSCs are undergoing asymmetric or symmetric cell kinetics. It gives an instantaneous measurement of important stem cell physiological states as well as an indication of the future growth rate of detected tissue-specific stem cells.

In one embodiment, the invention provides a method for distinguish the self-renewal pattern state of TSSCs in a tissue comprising: (a) obtaining a biological sample from the tissue; (b) contacting the biological sample with an antibody against an ASRA protein and/or CCSP wherein an antibody-protein complex is formed in situ; and (c) detecting the antibody-protein complex, wherein the presence of the antibody-protein complex in only one of the cells in a sister pair of cells originating from a single cell indicates that the TSSC is undergoing asymmetrical cell kinetics and wherein the absence of the antibody-protein complex indicate that the TSSC is undergoing symmetrical cell kinetics.

In one embodiment, the invention provides a method for determining the future growth rate of TSSCs in a tissue comprising determining the percent of asymmetrically cycling TSSC in the tissue, wherein less than the normal average TSSC fraction in the tissue indicates that the future growth rate is poor. The normal average TSSC fraction in the tissue ranges from 0.001% to 1% depending on the type of tissue.

In one embodiment, the invention provides a method for determining the future growth rate of TSSCs in a tissue comprising: (a) obtaining a biological sample from the tissue; (b) contacting the biological sample with an antibody against an ASRA protein or a CCSP wherein an antibody-protein complex is formed in situ; (c) detecting the antibody-protein complex; (d) counting the total number of cells in the biological sample and the number of cells comprising the antibody-protein complex; and (e) computing the percent of TSSC in the tissue by dividing the number of cell comprising the antibody-protein complex with the total number of cells in the biological sample, wherein less than the normal average TSSC fraction in the tissue indicates that the future growth rate is poor.

In one embodiment, the method for determining the future growth rate of TSSC in a tissue comprises culturing ex vivo the biological sample obtained from the tissue for a period of time before contacting the cultured biological sample with an antibody against an ASRA protein or a CCSP wherein an antibody-protein complex is formed in situ. In this embodiment, when the percent of TSSCs in the tissue is less than 10% of TSSCs in the tissue, it indicates that the future growth rate is poor.

In some embodiments of the methods described herein, the sample of TSSC, the sample of cells, the biological sample comprising TSSCs, or the aliquot sample of cells from the population of TSSCs is not contacted with an antibody that specifically binds to the ASRA protein or the CCSP. In some embodiments of the methods described herein, the sample of TSSCs, the sample of cells, the biological sample comprising TSSCs, or the aliquot sample of cells from the population of TSSCs is contacted with a small molecule, a drug or compound that can bind specifically to the ASRA protein or the CCSP wherein the small molecule, a drug or compound is not an antibody. In some embodiments of the methods described herein, the sample of TSSCs, the sample of cells, the biological sample comprising TSSCs, or the aliquot sample of cells from the population of TSSCs is contacted with a substrate, which the ASRA protein or the CCSP can chemically break down to by-products such as in a enzymatic chemical reaction.

In one embodiment, the computation of the percent of TSSCs is according to the formula I:

$$\text{Percent } TSSC = \frac{\text{No. of cells stained positive for } ASRA/CCSP \text{ in field of vision of counting}}{\text{Total No. of cells in field of vision of counting}} \times 100$$

In one embodiment, the methods described herein are applicable for any stem cells. In one embodiment, the methods described herein are applicable for any cell that undergoes asymmetric self-renewal. The asymmetric self-renewal detected by the present method, e.g., either CCSP-Cyto D or ASRA-Cyto D, is predicted to be both exclusive to and universal for TSSCs.

In one embodiment, the TSSC is a cancer stem cell. Cancer stem cells (CSCs) are cancer cells (found within tumors or hematological cancers) that possess characteristics associated with normal stem cells, specifically the ability to give rise to all cell types found in a particular cancer sample. CSCs are therefore tumorigenic (tumor-forming), perhaps in contrast to other non-tumorigenic cancer cells. CSCs can generate tumors through the stem cell processes of self-renewal and differentiation into multiple cell types. Such cells can persist in tumors as a distinct population and cause relapse and metastasis by giving rise to new tumors. Therefore, development of specific therapies targeted at CSCs holds hope for improvement of survival and quality of life of cancer patients, especially for sufferers of metastatic disease. The CXCR6, a pattern-specific asymmetrically locating ASRA in asymmetrically self-renewing cells, has been recently identified as human melanoma CSCs (Taghizadeh. et al., accepted for publication in PlosONE).

The efficacy of cancer treatments is, in the initial stages of testing, often measured by the ablation fraction of tumor mass (fractional kill) As CSCs would form a very small proportion of the tumor, this may not necessarily select for drugs that act specifically on the stem cells. The theory suggests that conventional chemotherapies kill differentiated or differentiating cells, which form the bulk of the tumor but are unable to generate new cells. A population of CSCs, which gave rise to it, could remain untouched and cause a relapse of the disease.

When a tumor is excised from a subject, the tumor, if large enough can be used to test or screen for drugs that can "kill" the CSCs within the tumor tissue. The tumor tissue can be divided to several smaller pieces wherein each piece is treated with a different drug or different dosage of drug for a fixed period of time ex vivo. One or two pieces of tumor tissue are kept without drug to serve as the control tissue. The drug that is most effective on the CSCs in tumor tissue ex vivo can be use to treat the subject.

In situations where the tumor is inoperable or too extensive for effective surgical excision, the subject can be treated with a drug and periodic tumor tissue biopsies can be taken out. The percent of CSCs in the tumor tissue biopsies can be determined for evaluation the efficacy of the drug treatment for the subject.

Figure 12:
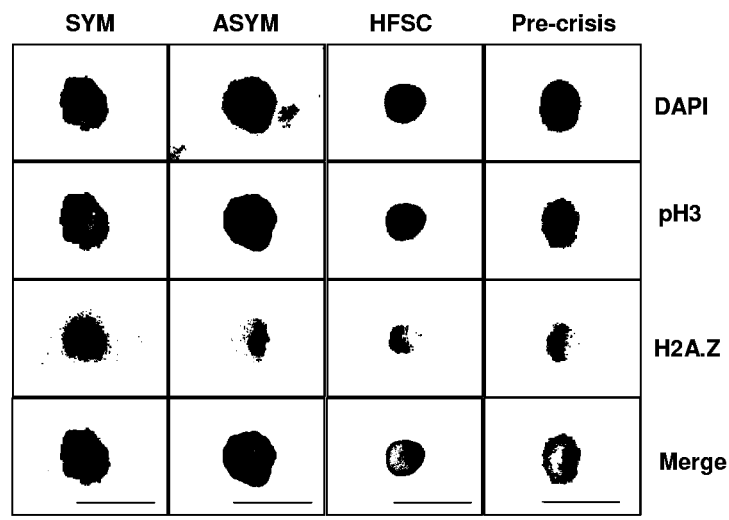
FIG. 12 shows that H2A.Z is asymmetrically localized in prophase nuclei detected by phosphorylated histone H3 in cultures undergoing asymmetric self-renewal. The inverted fluorescence images are shown. Scale bar=25 μm.

In some embodiments of the methods, after the contacting the cells with the antibody specific to the ASRA protein or CSSP of interest, the method further comprises detecting cells with the pattern-specific asymmetric localization of the antibody-protein complex; counting the total number of cells in the sample, a population of cells or a sample of tissue and counting the number of cell comprising the asymmetrically localized antibody-protein complex; and computing the percent of TSSC in the sample by dividing the number of cell comprising the asymmetrically localized antibody-protein complex with the total number of cells in the sample, a population of cells or a sample of tissue. The pattern-specific asymmetric localization is shown in FIG. 12 where the ASRA protein or CSSP of interest is detected in only one half of the prophase cell or in one sister of sister-pair of cells. The characteristic pattern-specific asymmetric localization of ASRA proteins is distinct from other "stem cell biomarkers" where the other "stem cell biomarkers" only exhibit up-regulated expression in stem cells (e.g., CD34, CD133).

In one embodiment, the expression levels of the ASRA proteins remain constant in TSSCs undergoing symmetrical or asymmetrical cell kinetics. These nuclear proteins are evenly distributed between the resultant TSSCs arising from symmetrical cell kinetics. In contrast, these proteins are localized predominantly in the sole TSSC arising from asymmetrical cell kinetics. An example of such an ASRA protein whose expression is not regulated and exhibits pattern-specific asymmetrical localization is H2A.Z.

In another embodiment, the expression levels of the ASRA proteins are very low or zero in TSSCs undergoing symmetrical cell kinetics but are up-regulated, sometimes significantly during asymmetrical cell kinetic. This increased amount of ASRA proteins are localized predominantly in the sole TSSC arising from asymmetrical cell kinetics. Examples of ASRA proteins whose expressions are up-regulated and exhibit pattern-specific asymmetrical localization are CXCR-6 and BTG-2.

In one embodiment, the computation of the percent of TSSCs is according to the formula II:

$$\text{Percent } TSSC = \frac{\text{(No. of cells stained positive for pattern-specific asymmetric localization of } (ASRA/CCSP \text{ in field of vision of counting)}}{\text{Total No. of cells in field of vision of counting}} \times 100$$

In one embodiment of the methods, the methods further comprise contacting the cells with an antibody specific for binding phosphorylated H3 protein (pH3), detecting cells with the antibody-protein complex; and counting the total number of pH3 positive cells in the sample.

In one embodiment of the methods, only pH3 positive cells are counted. Positive pH3 cells indicate that the cells are active mitotic cells since the methods relates to only dividing cells.

In one embodiment, the computation of the percent of TSSCs is according to the formula III:

$$\text{Percent } TSSC = \frac{\text{(No. of cells stained positive for pattern-specific asymmetric localization of } (ASRA/CCSP \text{ and also pH3 positive in field of vision of counting)}}{\text{Total No. of pH3 positive cells in field of vision of counting}} \times 100$$

Unless otherwise explained, all technical and scientific terms used herein have the same meaning as commonly understood by one of ordinary skill in the art to which this disclosure belongs. Definitions of common terms in cell biology and molecular biology can be found in The Encyclopedia of Molecular Biology, published by Blackwell Science Ltd., 1994 (ISBN 0-632-02182-9); Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006; and in Benjamin Lewin, Genes IX, published by Jones & Bartlett Publishing, 2007 (ISBN-13: 9780763740634).

Unless otherwise stated, the present invention is performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); Current Protocols in Immunology (CPI) (John E. Coligan, et. al., ed. John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol. 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Asymmetric Cell Kinetics

Asymmetric cell kinetics is a characteristic of somatic or adult stem cells. Adult somatic stem cells predominantly divide by asymmetric cell kinetics. While somatic stem cells also undergo limited symmetric divisions which produce two identical stem cells in developing adult tissues, such symmetric kinetics is restricted to periods of tissue expansion and tissue repair. Inappropriate symmetric somatic stem cell divisions evoke mechanisms leading to apoptosis of duplicitous stem cells. Some stem cells may also lie dormant for long periods before initiating division in response to specific developmental cues, as in reproductive tissues like the breast. However, the predominant cell kinetics state of somatic stem cells is asymmetric.

During asymmetric cell kinetics, one daughter cell divides with the same kinetics as its stem cell parent, while the second daughter gives rise to a differentiating, and ultimately non-dividing cell lineage. The second daughter may differentiate immediately or depending on the tissue, it may undergo a finite number of successive symmetric divisions to give rise to a larger pool of differentiating cells. The second daughter and its dividing progeny are called transiently amplifying cells or transit cells. Transit cell divisions ultimately result in mature, differentiated, terminally arrested cells. In tissues with high rates of cell turnover, the endpoint for differentiated terminal cells is programmed cell death by apoptosis.

Asymmetric cell kinetics evolved in vertebrates as a mechanism to insure tissue cell renewal with constant adult body mass while maintaining a limited set of stem cells. Mutations that disrupt asymmetric cell kinetics are an absolute requirement for the formation of a clinically significant tumor mass. In many ways, asymmetric cell kinetics provides a critical protective mechanism against the emergence of neoplastic growths that can be life threatening.

In culture, continued asymmetric cell kinetics of explanted stem cells is a major obstacle to their expansion in vitro. Ongoing asymmetric cell kinetics results in dilution and loss of an initial relatively fixed number of stem cells in starting tissue explants by the accumulation of much greater numbers of their terminally differentiating progeny. If a sample includes both exponentially growing transit cells as well as rare somatic stem cells, the growth of the exponentially dividing non-stem tissue cells will rapidly overwhelm the asymmetrically dividing somatic stem cells, leading to their dilution.

One regulator of asymmetric cell kinetics is the p53 tumor suppressor protein. Several stable cultured murine cell lines have been derived that exhibit asymmetric cell kinetics in response to controlled expression of the wild-type murine p53.

The p53 model cell lines have been used to define cellular mechanisms that regulate asymmetric cell kinetics. In addition to p53, the rate-limiting enzyme of guanine nucleotide biosynthesis, type II inosine-5'-monophosphate dehydrogenase (IMPDH II) is an important determinant of asymmetric cell kinetics. IMPDH II catalyzes the conversion of IMP to xanthosine monophosphate (XMP) for guanine ribonucleotide (rGNP) biosynthesis. This enzymatic reaction is rate-determining for the formation of the next metabolite in the pathway, GMP, from which all other cellular guanine nucleotides are derived. Accordingly, high levels of rGNPs promote exponential kinetics, whereas low levels of rGNPs promote asymmetric cell kinetics. Conditionally suppressing asymmetric cell kinetics can be achieved by enhancing guanine ribonucleotide biosynthesis, e.g., supplementing the culture media with guanine ribonucleotide precursors such as xanthosine (Xs), hypoxanthine (Hx) or xanthine (Xn), thereby expanding cellular pools of rGNPs.

Mechanisms which function downstream of the rGNPs to regulate cell kinetics (i.e., asymmetric versus exponential) can also be used to conditionally suppress asymmetric cell kinetics. These mechanisms include both genetic and/or pharmacological approaches, analogous to those described in detail herein. For example, one can enhance expression of a protein downstream of the rGNP biosynthesis pathway, if that protein inhibits asymmetric cell kinetics. Alternatively, one can down-regulate the expression of a protein downstream of the rGNP pathway if it promotes asymmetric cell kinetics.

Detection of ASRA Proteins and CCSPs

In one embodiment, the ASRA proteins and CCSPs are detected by antibodies.

The term "antibody" includes "antibody-based binding moiety", immunoglobulin molecules and immunologically active determinants of immunoglobulin molecules, e.g., molecules that contain an antigen-binding site that specifically binds, i.e., immunoreacts with, the disclosed ASRA proteins and CCSPs. The term "antibody-based binding moiety" is intended to include whole antibodies, e.g., of any isotype (IgG, IgA, IgM, IgE, etc), and includes fragments thereof which are also specifically reactive with the disclosed ASRA proteins and CCSPs. Antibodies can be fragmented using conventional techniques. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')$_2$, Fab', Fv, dAbs, single chain antibodies (scFv) containing a VL and VH domain joined by a peptide linker, di-scFv and other engineered form of monoclonal antibodies. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety is detectably labeled.

"Labeled antibody", as used herein, includes antibodies that are labeled by a detectable means and include, but are not limited to, antibodies that are enzymatically, radioactively, fluorescently and chemiluminescently labeled. Antibodies can also be labeled with a detectable tag, such as c-Myc, HA, VSV-G, HSV, FLAG, V5, or HIS.

In one preferred embodiment, the antibody is detectably labeled by linking the antibody to an enzyme. The enzyme, in turn, when exposed to its substrate, will react with the substrate in such a manner as to produce a chemical moiety which can be detected, for example, by fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radio-immune assays. The radioactive isotope can be detected by such means as audioradiography. Isotopes which are particularly useful for the purpose of the present invention are $^3$H, $^{131}$I, $^{35}$S, $^{14}$C and preferably $^{125}$I.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

In an "immunohistochemistry assay" a section of tissue is tested for specific proteins by exposing the tissue to antibodies that are specific for the protein that is being assayed. In immunocytochemistry, a sample of individual cells is tested. The antibodies are then visualized by any of a number of methods to determine the presence of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art, e.g., described in the World Wide Website of "protocol-online" period "org".

In one embodiment, the methods of the invention comprise using antibodies or anti-sera against CXCR-6, BTG2, LGR5 and H2A.Z. In another embodiment, the methods of the invention comprise using antibodies or anti-sera against CCSPs such as cyclin A, cyclin D, cyclin E, CDKN1A, TK, Ki67, TS, DHFR and the GAS-X proteins. The antibodies for use in the present invention can be obtained from a commercial source such as ABCAM® as disclosed herein. The antibodies can be polyclonal or monoclonal antibodies. Alternatively, antibodies can be raised against CXCR-6, BTG2, LGR5, H2A.Z, cyclin A, cyclin D, cyclin E, CDKN1A, TK, Ki67, TS, DHFR and the GAS-X proteins. Methods for the production of enzyme antibodies well known in the art, e.g., those disclosed in PCT publication WO 97/40072 and U.S. Application No. 2002/0182702, which are incorporated herein by reference in their entirety.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702, 892 (U.S.A. Health & Human Services) and WO 01/18058 (Novopharm Biotech Inc.) disclose bacteriophage display libraries and selection methods for producing antibody binding domain fragments.

Detection of antibodies can be achieved by direct labeling of the antibodies themselves, with labels including a radioactive label such as $^3$H, $^{14}$C, $^{35}$S, $^{125}$I, or $^{131}$I, a fluorescent label, a hapten label such as biotin, or an enzyme such as horse radish peroxidase or alkaline phosphatase. Alternatively, unlabeled primary antibody is used in conjunction with labeled secondary antibody, comprising antisera, polyclonal antisera or a monoclonal antibody specific for the primary antibody. In one embodiment, the primary antibody or antisera is unlabeled, the secondary antisera or antibody is conjugated with biotin and enzyme-linked strepavidin is used to produce visible staining for histochemical analysis.

In other embodiments, the ASRA protein and/or CCSP is detected by methods that do not require antibodies against the ASRA protein and/or CCSP. In one embodiment, the ASRA protein and/or CCSP is detected by binding of a small molecule, drug or compound to the ASRA protein and/or CCSP in the complex. In some embodiments, the small molecule, drug or compound can be any entity, organic or inorganic. The small molecule, drug or compound can be detectable labeled as described herein. In one embodiment, the ASRA protein and/or CCSP is an enzyme and the ASRA protein is detected by the enzymatic activity of the ASRA protein, comprising contacting the ASRA protein in the complex with an substrate for the ASRA protein and measuring the disappearance of the substrate or the accumulation of a by-product. In one embodiment, the substrate is detectable labeled as described herein or can be detected by absorption of energy at a specific wavelength. For example, if an ASRA protein or CCSP is an enzyme; in situ enzymatic detection can be used to detect its presence. In one embodiment, the ASRA protein and/or CCSP in the complex is detected by imaging mass spectrometry in situ in tissue sections or cell preparations. Methods of such imaging are well known in the art, e.g. as described by Philippe Hallégot et al., J. Invest. Dermat., 2004, 122:381-386; Burnum K E, et al., Endocrinology. 2008, 149:3274-8; Ikuko Yao, et al., 2008 in Proteomics, Special Issue: Focus on imaging mass spectrometry, Volume 8 Issue 18, Pages 3692-3701, Publisher WILEY-VCH Verlag GmbH & Co. KGaA, Weinheim; and Praneeth D., et al., Anal. Chem., 2007, 79:508-514.

DEFINITIONS OF TERMS

As used herein, the term "asymmetric self-renewal" in reference to tissue specific stem cells refers to the unique characteristic wherein when such a stem cell undergo cell division to produce two daughter cells, one of these daughter cell inherits the stem cell properties while the second daughter cell develops to a differentiated cell which may divide further to produce progeny of differentiated cells.

In one embodiment, as used herein, the term "pattern-specific asymmetrical localization" when used in reference to an ASRA protein refers to a ASRA protein whose (1) protein expression undergoes little changes during asymmetric or symmetric cell division, or there is little or no protein expression during symmetric cell division but the expression is up-regulated when the cell undergoing asymmetrical cell kinetics. In another embodiment, the term "pattern-specific asymmetrical localization" when used in reference to an ASRA protein refers to a ASRA protein that localizes predominantly to the sole mother stem cell during asymmetrical cell kinetics of a TSSC but then is evenly distributed to or is absent in both the stem cells arising from a symmetric cell division of a TSSC.

As used herein, the term "comprising" means that other elements can also be present in addition to the defined elements presented. The use of "comprising" indicates inclusion rather than limitation.

The term "consisting of" refers to methods, and respective components thereof as described herein, which are exclusive of any element not recited in that description of the embodiment.

As used herein, the term "expanding" refers to increasing the number of like cells through cell division (mitosis). The term "proliferating" and "expanding" are used interchangeably.

The term "contacting" or "contact" as used herein as in connection with contacting a TSSC, a population of cells comprising at least one TSSC, a population of TSSCs, a sample of cells comprising at least one TSSC, a sample of TSSCs, a sample or section of tissue with antibody, drug, compound or agent as disclosed herein, includes subjecting the cell to a culture media, which comprises the antibody, drug, compound or agent.

The term "pluripotent" as used in reference to a "pluripotent cell" herein refers to a cell with the capacity, under different conditions, to differentiate to cell type's characteristic of all three germ cell layers (endoderm, mesoderm and ectoderm). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "pluripotency" or a "pluripotent state" as used in reference to a "pluripotent cell" herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of multipotent cells include adult somatic stem cells, such as for example, hematopoietic stem cells and neural stem cells, hair follicle stem cells, liver stem cells etc. Multipotent means a stem cell may form many types of cells in a given lineage, but not cells of other lineages. For example, a multipotent blood stem cell can form the many different types of blood cells (red, white, platelets, etc.), but it cannot form neurons; cardiovascular progenitor cell (MICP) differentiation into specific mature cardiac, pacemaker, smooth muscle, and endothelial cell types; pancreas-derived multipotent progenitor (PMP) colonies produce cell types of pancreatic lineage (cells that produces insulin, glucagon, amylase or somatostatin) and neural lineage (cells that are morphologically neuron-like, astrocytes-like or oligodendrocyte-like).

The term "differentiated cell" is meant any primary cell that is not, in its native form, pluripotent as that term is defined herein. The term a "differentiated cell" also encompasses cells that are partially differentiated, such as multipotent cells (e.g., adult somatic stem cells). It should be noted that placing many primary cells in culture can lead to some loss of fully differentiated characteristics. Thus, simply culturing such cells are included in the term differentiated cells and do not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

The term "stem cell" as used herein, refers to an undifferentiated cell that is capable of proliferation and giving rise to more progenitor cells having the ability to generate a large number of mother cells that can in turn give rise to differentiated, or differentiable daughter cells. The ability to differentiate is the potential to develop into other cell types. A totipotent stem cell (e.g., fertilized egg) can develop into all cell types including the embryonic membranes. A pluripotent stem cell can develop into cells from all three germinal layers (e.g., cells from the inner cell mass). Other cells can be oligopotent, bipotent or unipotent (e.g., mast cell precursor and sperm stem cells) depending on their ability to develop into few, two or one other cell type(s). The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. Unipotent stem cells produce non-stem cell progeny that differentiate into only one cell type (e.g., sperm stem cells, which produce only sperm; and lens stem cells which produce only lens-forming cells).

In one embodiment, the term "stem cell" refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells can be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stemness."

Self-renewal is the other classical part of the stem cell definition, and it is essential as used in this document. Self-renewal is the ability of stem cells to divide and produce more stem cells. During early development of a multi-cellular organism, the cell division is symmetrical i.e., each cell divides to gives rise to daughter cells each with the same potential. Later in development, the cell divides asymmetrically where one of the daughter cells produced is also a stem cell and the other daughter cell is a more differentiated cell. Therefore, in a developed multi-cellular organism, an indication of self-renewal is asymmetric division, with one daughter retaining the same stem state as the parent cell and the other daughter expressing some distinct other specific function and phenotype.

Under in vitro conditions, isolated stem cells exhibit characteristics that are not exactly similar to their characteristics in vivo, e.g., embryonic stem cells and induced pluripotent stem cells. For example, they self-renew exclusively in one cell culture condition, they can differentiate exclusively and completely in another cell culture condition, but they do not do both simultaneously, i.e., differentiate and self renew simultaneously. Under these in vitro conditions, differentiation and self renewal are mutually exclusive. Embryonic stem cells and induced pluripotent stem cells can be propagated for long periods in culture with medium cocktails that prevent them from undergoing differentiation. When the cocktails are removed, they initiate uncontrolled varied differentiation programs that convert them completely to a non-pluripotent state. Thus, embryonic "stem cells" and induced pluripotent "stem cells" cannot be recovered from their differentiated cultures.

Tissue-specific stem cells are stem cells that can be classified by their biological function and they appear later in development. They can self-renew exclusively under some culture conditions (but with constraints), however their default under normal cell culture conditions is simultaneous self-renewal and production of progeny cells that undergo differentiation (i.e., asymmetric self-renewal). Accordingly, TSSCs can always be recovered even from conditions that promote complete differentiation of their lineage committed differentiating sister cells.

In vivo, epiblasts, the natural precursors of embryonic stem cells, which are artificial, initiate a developmental program that yields diversified TSSCs that support the diverse tissues of the body by asymmetric self-renewal. However, no epiblasts remain in mature body tissues. It is currently unknown whether differentiating cultures of embryonic stem cells and induced pluripotent stem cells produce asymmetrically self-renewing TSSCs; but if they do, the TSSCs likely are not the original pluripotent artificial "stem cells" that originated the cultures. Those are lost to their own differentiation.

In the context of cell ontogeny, the term "differentiate", or "differentiating" is a relative term meaning a "differentiated cell" is a cell that has progressed further down the developmental pathway than its precursor cell. For example, a muscle satellite cell is a TSSC that had developed from a mesenchymal stem cell. In other words, the muscle satellite cell has differentiated from a mesenchymal stem cell, its precursor cell.

The term", "tissue specific stem cell", "adult stem cell" or "ASC" is used to refer to any multipotent stem cell derived from non-embryonic tissue, including fetal, germinal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary tissue specific stem cell or adult stem cells include liver stem cells, hair follicle stem cells, neural stem cells, neural crest stem cells, mesenchymal stem cells, hematopoietic stem cells, and pancreatic stem cells. As indicated above, stem cells have been found resident in virtually every tissue. "Adult stem cell", "tissue specific stem cell" and "somatic stem cells" are used interchangeably.

The present invention can be defined in any of the following alphabetized paragraphs:

[A] A method for determining a percent of tissue specific stem cells (TSSC) in a tissue comprising:
   a. obtaining a biological sample from the tissue;
   b. contacting the biological sample with an antibody against an asymmetric self-renewal associated (ASRA) protein wherein an antibody-protein complex is formed in situ;

c. detecting the antibody-protein complex;
d. counting the total number of cells in the biological sample and the number of cells comprising the antibody-protein complex; and
e. computing the percent of TSSC in the tissue by dividing the number of cell comprising the antibody-protein complex with the total number of cells in the biological sample.

[B] A method for determining a percent of tissue specific stem cells (TSSC) in a sample of cells comprising:
 a. contacting a sample of cells with an antibody against an asymmetric self-renewal associated (ASRA) protein wherein an antibody-protein complex is formed in situ;
 b. detecting the antibody-protein complex;
 c. counting the total number of cells in the sample and the number of cell comprising the antibody-protein complex; and
 d. computing the percent of TSSC in the sample by dividing the number of cell comprising the antibody-protein complex with the total number of cells in the sample.

[C] A method of monitoring an expansion of tissue specific stem cells (TSSC), the method comprising:
 a. obtaining a biological sample containing TSSC at least two time points, a first and a second time point;
 b. contacting an aliquot of TSSC obtained at least two time point with an antibody against an asymmetric self-renewal associated (ASRA) protein wherein an antibody-protein complex is formed in situ;
 c. detecting the antibody-protein complex;
 d. counting the total number of cells and the number of cells comprising the antibody-protein complex in each aliqout;
 e. computing the percent of TSSC in each aliqout by dividing the number of cells comprising the antibody-protein complex with the total number of cells in the aliqout of the respective time point, wherein if the percent of TSSC is greater in the second time point compared to the first time point indicates that the TSSC is expanding.

[D] A method of determining efficacy of a drug on a culture of tissue specific stem cells (TSSC) in ex vivo, the method comprising:
 a. culturing, in parallel, a population of TSSC in the presence of a drug and a population of TSSC in the absence of the drug;
 b. obtaining a sample of TSSC from each of the populations;
 c. contacting the samples of TSSC with an antibody against an asymmetric self-renewal associated (ASRA) protein wherein an antibody-protein complex is formed in situ;
 d. detecting the antibody-protein complex;
 e. counting the total number of cells and the number of cells comprising the antibody-protein complex in each sample;
 f. computing the percent of TSSC in each sample by dividing the number of cells comprising the antibody-protein complex with the total number of cells in the respective sample, wherein if the percent of TSSC in the sample in the presence of the drug is greater than the percent of TSSC in the sample in the absence of the drug indicates that the culture is expanding and the drug is a positive modulator of TSSC, and if the number of TSSC in the sample in the presence of the drug is less than the percent of TSSC in the sample in the absence of the drug indicates that the culture is decreasing and the drug is a negative modulator of TSSC; and wherein if the percent of TSSC in the sample in the presence of the drug is about equal to the percent of TSSC in a sample in the absence of the drug indicates that the drug has no effect on the growth and expansion of the TSSC.

[E] A method of determining efficacy of a drug on tissue specific stem cells (TSSC) in vivo, the method comprising:
 a. administering the drug to a subject;
 b. contacting a sample of TSSC from the subject with an antibody against an asymmetric self-renewal associated (ASRA) protein wherein an antibody-protein complex is formed in situ;
 c. detecting the antibody-protein complex;
 d. counting the total number of cells and the number of cells comprising the antibody-protein complex in the sample;
 e. computing the percent of TSSC in the sample by dividing the number of cells comprising the antibody-protein complex with the total number of cells in the respective sample, wherein if the percent of TSSC is greater than a control indicates that the TSSC is expanding in vivo and the drug is a positive modulator of TSSC, wherein the percent of TSSC is less than a control indicates that the TSSC is decreasing and the drug is a negative modulator of TSSC, and wherein the percent of TSSC is about the equal with the control indicates that the drug has no effect on the expansion of TSSC in vivo.

[F] A method of prognosing a therapeutic efficacy of a population of tissue specific stem cells (TSSC) for transplantation, the method comprising:
 a. contacting an aliqout sample of cells from the population of TSSC with an antibody against an asymmetric self-renewal associated (ASRA) protein wherein an antibody-protein complex is formed in situ;
 b. detecting the antibody-protein complex;
 c. counting the total number of cells and the number of cells comprising the antibody-protein complex in the sample;
 d. computing the percent of TSSC in the sample by dividing the number of cells comprising the antibody-protein complex with the total number of cells in the respective sample, wherein the percent of TSSC is greater than a control indicates that the population of TSSC is likely therapeutically effective.

[G] The method of any of paragraphs A-F wherein the ASRA protein is a pattern-specific asymmetrically located protein in a cell undergoing asymmetrical cell kinetics.

[H] The method of any of paragraphs A-G, wherein only the number of cells comprising pattern-specific asymmetrically located antibody-protein complex are counted and used in the computation of the percent TSSCs.

[I] The method of any of paragraphs A-H, wherein the ASRA protein is selected from a group consisting of CXCR-6, BTG2, or H2A.Z.

[J] The method of any of paragraphs A-I, wherein the sample of TSSCs is grown and cultured in low cell density of about $1 \times 10^3$ cells/ml.

[K] The method of any of paragraphs A-I, wherein the sample of TSSCs are grown and cultured in high cell density of about $1 \times 10^5$ cells/ml to about $5 \times 10^6$ cell/ml.

[L] The method of any of paragraphs A-K, wherein the sample of TSSCs is fixed and permeabilized prior contacting with the antibody against an ASRA.

[M] The method of any one of paragraphs C, G-L, wherein the TSSC is expanded in vivo.

[N] The method of any of paragraphs C, G-L, wherein the TSSC is expanded ex vivo.

[O] The method of any one of paragraphs C, G-N, wherein the TSSC is expanded in culture.

[P] The method any one of paragraphs E, G-0, wherein the control is the percent of TSSC in a sample from the subject prior to administration of the drug or at an earlier time point, wherein the number of TSSC in the sample is determined by the same method as used for computing the percent of TSSC after administration of drug.

[Q] The method of any one of paragraphs C—P, wherein the TSSC is a hematopoietic stem cell (HSC) or a hair follicle stem cell (HFSC).

[R] The method of paragraph Q, wherein the TSSC is expanded and wherein the TSSC is a HSC and the transplantation is bone marrow transplantation or the TSSC is a HFSC for hair replacement therapy.

[S] The method of any one of paragraphs F, G-0, Q-R, wherein the TSSC is obtained from a source selected from a group consisting of cord blood, bone marrow and mobilized peripheral blood.

[T] The method of paragraph S, wherein the TSSC is expanded ex vivo.

[U] A method for determining a percent of TSSC in a sample of cells comprising:
  a. contacting a sample of cells with an antibody against a CCSP wherein an antibody-protein complex is formed in situ;
  b. detecting the antibody-protein complex;
  c. counting the total number of cells in the sample and the number of cell comprising the antibody-protein complex; and
  d. computing the percent of TSSC in the sample by dividing the number of cell comprising the antibody-protein complex with the total number of cells in the sample.

[V] A method for determining a percent of TSSC in a tissue comprising:
  a. obtaining a biological sample from the tissue;
  b. contacting the biological sample with an antibody against a CCSP wherein an antibody-protein complex is formed in situ;
  c. detecting the antibody-protein complex;
  d. counting the total number of cells in the biological sample and the number of cells comprising the antibody-protein complex; and
  e. computing the percent of TSSC in the tissue by dividing the number of cell comprising the antibody-protein complex with the total number of cells in the biological sample.

[W] The method of paragraphs U or V, wherein the CCSP is a pattern-specific asymmetrically located protein in a cell undergoing asymmetrical cell kinetics.

[X] The method of any of paragraphs U-W, wherein only the number of cells comprising pattern-specific asymmetrically located antibody-protein complex are counted and used in the computation of the percent TSSCs.

[Y] The method of any one of paragraphs U-X, wherein the CCSP is selected from a group consisting of cyclin A, cyclin D1, cyclin E, CDKN1A, TK, Ki67, TS, DHFR and the GAS-X proteins.

This invention is further illustrated by the following example, which should not be construed as limiting. The contents of all references cited throughout this application, as well as the figures and table are incorporated herein by reference.

EXAMPLES

The inventors have developed a method for detecting and counting TSSCs that (1) does not require BrdU uptake; (2) can be used with cytochalasin D to verify sister-sister relationship for asymmetric self-renewal detection; (3) that uses proteins encoded by asymmetric self-renewal associated (ASRA) genes as indicators of the unique division pattern-specific markers of TSSCs; and (4) that involves direct identification of chromosomes that contain immortal DNA strands in naturally-occurring mitotic cells. This method has been verified with specific TSSC biomarkers for intestinal epithelial stem cells (IESC) and hair follicle stem cells (HFSC) in the examples below.

Materials and Methods
Methods Summary

Ind-8 and Con-3 cells were maintained as previously described is Rambhatla et al. 2005 and Rambhatla et al., 2001. HFSC strain 3C5 and 5B8 cells were clonally derived by the SACK method as described in Sherley and King, 2010 and also described below. Indirect ISIF detection of cyclin A, H2A.Z, and LGR5 was integrated with previously described methods ("daughter pair analysis") (Merok at al., 2002 and Lee at al., 2003) to develop the SP and CD assays for self-renewal pattern. The specific indirect ISIF procedures are detailed below. Mitotic cell analyses were performed with slides coated with collagen IV and indirect in situ immunofluorescence (ISIF) with anti-α-tubulin and anti-H2A.Z specific antibodies. In histological sections, mitotic cells were identified with specific antibodies for phosphorylated histone H3 (pH3), a mitotic cell biomarker. Mitotic cells undergoing immortal DNA strand co-segregation were identified by BrdU retention, which was quantified by the quenching of Hoechst 33258 (Sigma Aldrich, St. Louis, Mo.) fluorescence, as described (Merok at al., 2002) with modifications detailed below. Fisher's exact tests were performed at the World Wide web site of Daniel Soper. Statistical parameters for Hoechst 33258 fluorescence intensity histograms were determined using the NIH ImageJ program. The Kolmogorov-Smirnov test for distributions was performed at the World Wide web site of the physics department of the College of Saint Benedict & Saint John's University. Linear regression analyses were performed with Excel 2008 software (Microsoft Corp., Redmond, Wash.) and GraphPad Prism (GraphPad Software, LaJolla, Calif.) statistical packages.

Clonal Derivation of SACK-Expanded HFSC Strains

After $CO_2$-asphyxiation, the facial area of 4- to 6-week old inbred FVB/NTac mice (Taconic) was cleaned with 70% ethanol. The upper lip region was excised, and the inner surface was exposed (Kobayashi et al., 1993 and Oliver, 1966). Each lip region was divided into two whisker pads and placed in a 35-mm Petri dish containing sterile phosphate buffered saline (PBS). Under a dissecting microscope, subcutaneous fat and connective tissue were removed to expose individual hair follicles (Jahoba and Oliver, 1981). Each vibrissa was then removed from the whisker pad by grasping the neck region closest to the inner surface of the epidermis with fine forceps and pulling it away from the pad. Detached follicles were placed in a 35-mm dish containing sterile media.

After cutting off protruding whisker shafts, excised follicles was transferred to a dish containing sterile medium which consisted of a 3:1 mixture of DMEM and Ham's F12 media (Kobayashi et al., 1993) supplemented with 10% dialyzed fetal bovine serum (DFBS), 1% penicillin/streptomycin, 10 ng/mL epidermal growth factor (Kobayashi et al., 1993 and Hoeller et al., 2001) and 400 µM xanthine. The contents of the dish containing the isolated follicles were filtered through a 70-µm filter. The follicles were then placed in a 50-mL conical tube containing 1.0 mL of trypsin (0.05%) and incubated at 37° C. for five minutes to remove any cells attached to the outer surface of follicles. The trypsin was inactivated with 4 mL control medium, and the follicles were removed by filtration onto a 70-µm filter. The digested follicles were placed in a 35-mm dish with sterile medium and transversely incised in the vicinity of the bulge region to expose their interiors. Three incised follicles were transferred to a single well of a 24-well plate containing 2 mL of medium to establish SACK expansion cultures at 37° C. in a humidified incubator with a 5% $CO_2$ atmosphere.

The primary 24-well cultures of hair follicle cells were grown to confluency. During this period, 1.0 mL of medium was removed and replenished every four days. When confluent, cells were treated with trypsin-PBS (0.025%) to detach, and the entire content of single wells was transferred to a 25-$cm^2$ flask. The entire 5-mL volume of culture medium was replaced every four days until flasks were confluent. When confluent, cells were trypsinized and transferred in their entirety to a 75-$cm^2$ flask. Again, culture medium was changed every four days until cultures reached confluency. At this point, independently established cultures were cryo-preserved and sub-cloned by limiting dilution to derive HFSC strains, including 3C5 and 5B8.

Self-Renewal Pattern Assays

To initiate analyses, studied cells were plated at an input cell number:cell attachment area:medium volume ratio of $1 \times 10^5$:75 $cm^2$:20 mls, cultured over a 2-3 day period to achieve ~25% confluency, and then replaced with fresh culture medium. Sixteen to 24 hours later, when cultures were ~50% confluent, cells were trypsinized and used to conduct self-renewal pattern and immortal DNA strand co-segregation analyses.

Low Cell Density Sister Pair (SP) Analysis

For low-density SP analyses, trypsinized cells were plated at 500 cells/$cm^2$ in 2-well LAB-TEK® chamber slides (Nunc, Inc., Naperville, Ill.) in Zn-free medium. Five hours later, for Con-3 and Ind-8 cells, the culture medium were replaced with either Zn-free medium or medium supplemented to 65 µM $ZnCl_2$. For HFSC analyses, the culture medium was replaced with either xanthine-free medium or medium supplemented with 400 µM xanthine. Twenty hours later, slides were washed with ice-cold phosphate buffered saline (PBS) and immediately fixed for 15 minutes at room temperature in PBS containing 3.7% formaldehyde. After three washes in PBS, the cells were permeabilized with 0.2% Triton X-100 (v/v in PBS) at room temperature for 10 minutes and afterwards washed once with PBS.

Thereafter, cells were blocked with PBS containing 10% goat serum for 1 hour at room temperature. They were then incubated overnight at 4° C. in a humidified chamber with a mouse anti-mouse cyclin A monoclonal antibody (ABCAM, Inc., Cambridge, UK) diluted 1:100 in PBS containing 2% goat serum. After five rinses in PBS containing 0.5% bovine serum albumin (BSA), the cells were incubated for 1 hour at room temperature with ALEXA FLUOR® 568-conjugated goat anti-mouse IgG (INVITROGEN, Inc., Carlsbad, Calif.) diluted 1:300 in blocking solution (10% goat serum; SIGMA-ALDRICH Co., St. Louis, Mo.). Next, the cells were washed five times with PBS containing 0.5% BSA.

Cells stained for cyclin A detection were subsequently incubated in the same manner with either rabbit anti-mouse H2A.Z (C-terminal peptide) polyclonal antibody (Cell Signaling Technology, Inc., Danvers, Mass.) diluted 1:200 or goat anti-mouse LGR5 polyclonal antibody (Santa Cruz, Biotechnology, Inc., Santa Cruz, Calif.) diluted 1:50. A sheep polyclonal antibody against full-length H2A.Z (Santa Cruz, Biotechnology, Inc., Santa Cruz, Calif.) gave similar results. These antibodies were followed with ALEXA FLUOR® 488-conjugated goat anti-rabbit IgG (INVITROGEN, Inc., Carlsbad, Calif.) diluted 1:300 or ALEXA FLUOR® 488-conjugated donkey anti-goat IgG (INVITROGEN, Inc., Carlsbad, Calif.) diluted 1:300, respectively. After washing, the cells were mounted with 4'-6-diamido-2-phenylindole (DAPI)-containing VECTASHIELD® mounting media (Vector Laboratories, Inc., Burlingame, Calif.). Epifluorescence images were captured with a Leica DMR microscope and Leica DC300F digital camera system. Control analyses that omitted anti-cyclin A, anti-H2A.Z, and anti-LGR5 antibodies, in combination or separately, were evaluated to ensure that all detected fluorescence required specific antibodies.

High Cell Density Cytochalasin D (CD) Analysis

For high-density binucleated cell analysis with CD treatment, cells were plated at 2,000 cells/$cm^2$ in 2-well LAB-TEK® chamber slides (Nunc, Inc., Naperville, Ill.). Thereafter, cells were cultured, fixed, and prepared for dual indirect ISIF as for SP analyses except, before fixation, they were cultured in their respective media supplemented with 2 µM cytochalasin D (Sigma-Aldrich Co., St. Louis, Mo.) for 14 hours.

Mitotic Cell Analyses

Analysis with α-Tubulin In Vitro

For detection of H2A.Z in mitosis, trypsinized cells were plated in Zn-free medium at 1000 cells/$cm^2$ in 2-well LAB-TEK® chamber slides (Nunc, Inc., Naperville, Ill.) coated with 1 µg/$cm^2$ collagen IV (BD Biosciences, San Jose, Calif.) per the supplier's instructions. Five hours later, for Con-3 and Ind-8 cells, the culture medium were replaced with either Zn-free medium or medium supplemented to 65 µM $ZnCl^2$; or, for HFSC analyses, either xanthine-free medium or medium supplemented with 400 µM xanthine. Twenty hours later, cells were washed with ice-cold PBS and immediately fixed for ISIF as described for SP and CD analyses with the following modifications. Dual indirect ISIF was performed for H2A.Z and α-tubulin with the following sequence of antibodies and blocking solutions: rabbit anti-mouse H2A.Z (C-terminal peptide) polyclonal antibody (Cell Signaling Technology, Inc., Danvers, Mass.) diluted 1:200 in PBS containing 2% goat serum; and ALEXA FLUOR® 488-conjugated goat anti-rabbit IgG (INVITROGEN, Inc., Carlsbad, Calif.) diluted 1:300 in blocking solution. Next, the cells were washed five times with PBS containing 0.5% BSA followed by anti-mouse α-tubulin mouse monoclonal antibody (Sigma Aldrich, St. Louis, Mo.) diluted 1:1,000 in 2% goat serum; and ALEXA FLUOR® 568-conjugated goat anti-mouse IgG (INVITROGEN, Inc., Carlsbad, Calif.) diluted 1:500 in blocking solution. After washing, the cells were mounted with 4'-6-diamido-2-phenylindole (DAPI)-containing VECTASHIELD® mounting media (Vector Laboratories, Inc., Burlingame, Calif.). Epifluorescence images were captured with a Leica DMR microscope and Leica DC300F digital camera system. Control analyses that omitted anti-H2A.Z and anti-α-tubulin antibodies, together or separately, were evaluated to ensure that all detected fluorescence required specific antibodies.

Analysis with Phosphorylated Histone H3 (pH3) In Vitro

For mitotic cell analysis of H2A.Z with phosphorylated histone H3 (pH3; phospho-S10), Con-3 cells, Ind-8 cells, HFSCs were plated and maintained as for mitotic cell analysis of H2A.Z with α-tubulin as a mitotic cell biomarker. The cells were then washed with ice cold PBS and immediately fixed for 15 minutes at room temperature in PBS containing 3.7% formaldehyde. Thereafter, dual indirect ISIF analyses were performed for H2A.Z and pH3 as described for mitotic cell analysis of H2A.Z and α-tubulin. In brief, after blocking, cells were incubated overnight at 4° C. in a humidified chamber with an anti-rabbit H2A.Z polyclonal antibody (Cell Signaling Technology, Inc., Danvers, Mass.) diluted 1:200 in PBS containing 2% goat serum. After five rinses in PBS containing 0.5% bovine serum albumin (BSA), the cells were incubate for 1 hour at room temperature with ALEXA FLUOR® 488-conjugated goat anti-rabbit IgG (INVITROGEN, Inc., Carlsbad, Calif.), diluted 1:300 in the blocking solution. Next, the cells were washed five times with PBS containing 0.5% BSA. Cells stained for H2A.Z detection were subsequently incubated in the same manner with anti-mouse anti-pH3 monoclonal antibody (ABCAM, Inc., Cambridge, Mass.) at a 1:1,000 dilution followed by ALEXA FLUOR® 568-conjugated goat anti-mouse IgG (INVITROGEN, Inc., Carlsbad, Calif.) diluted 1:500. After washing, the cells were mounted with 4'-6-diamido-2-phenylindole (DAPI)-containing VECTASHIELD® mounting media (Vector Laboratories, Inc., Burlingame, Calif.). Epifluoroescence images were captured with a Leica DMR microscope and Leica DC300F digital camera system. Pair-wise control analyses that omitted anti-H2A.Z and anti-pH3 antibodies separately and together were evaluated to ensure that all detected fluorescence required the specific antibodies.

Analysis with Phosphorylated Histone H3 (pH3) in Histological Sections

For tissue analyses, sections (10 μm) of paraffin-embedded FVB mouse (Taconic Farms, Inc., Hudson, N.Y.) skin that included hair follicles were cut on a Leica RM2255 microtome (Leica Microsystems, Inc., Bannockburn, Ill.) and picked up on Superfrost/Plus glass slides (Fisher Scientific, Inc., Pittsburgh, Pa.). For indirect ISIF, sections were deparaffinized in xylene and re-hydrated with a descending series of ethanol solutions (100%, 95%, 90%, 80%, 70%). Sections were then washed three times with PBS and incubated with phosphate buffered sodium citrate solution (0.01M, pH 7.4) for 20 min in a steamer to expose epitopes blocked during fixation and embedding. After washing in PBS, the sections were permeabilized with 0.2% Triton X-100 (v/v in PBS) at room temperature for 10 minutes and afterwards washed once with PBS. Thereafter, sections were blocked with 10% goat serum for 1 hour at room temperature and dual indirect ISIF analyses were performed for H2A.Z and pH3 as described for cultured cells.

Immortal DNA Strand—H2A.Z Analyses

For BrdU-retention/Hoechst quenching detection of immortal DNA strands, Ind-8 cells were plated in Zn-free medium at 125 cells/cm² in 2-well LAB-TEK® chamber slides (Nunc, Inc., Naperville, Ill.) coated with 1 μg/cm² collagen IV (BD Biosciences, San Jose, Calif.) per the supplier's instructions. Twenty hours later, the medium was replaced with both Zn-free and BrdU-free medium (i.e., control culture medium) or Zn-free medium containing 20 μM BrdU. After 24 hours, all cells were rinsed and replaced with BrdU-free medium supplemented to 65 μM $ZnCl_2$ to induce asymmetric self-renewal and immortal DNA strand co-segregation. 96 hours later (~4 generation periods), cells were washed with ice-cold PBS and immediately fixed for ISIF as described for SP and CD analyses with the following modifications. Dual indirect ISIF was performed for H2A.Z and α-tubulin was performed as described above. However, after the final PBS wash, the DNA of cells was counterstained with 0.5 μg/ml of Hoechst 33258 (SIGMA ALDRICH, St. Louis, Mo.) and mounted with Fluoromount-G (SouthernBiotech, Birmingham, Ala.). Epifluorescence images of mitotic cells were captured with a Leica DMR microscope and Leica DC300F digital camera system. The mean pixel intensity of UV-excited Hoechst fluorescence of segregating chromosome complements in late metaphase and anaphase cells was quantified using NIH ImageJ software.

Example 1

Assay 1

Detection of Asymmetrically Self-Renewing TSSCs with Known Cell Cycle-Specific Proteins (CCSPs)

To detect asymmetric self-renewal, we employed indirect ISIF detection in two related single-cell self-renewal pattern assays. In the first, the sister pair assay (SP), cells are plated at a sufficiently low density to allow delineation of sister cells based on their close proximity after division (Lee at al., 2003). In the second, cells are analyzed after division in the presence of cytochalasin D (CD) (Merok et al., 2002 and Rambhatla et al., 2005). CD prevents cytokinesis, but does not prevent nuclear division. The binucleated cells produced provide a definite comparison of sister nuclei.

Low cell density CCSP-SPA (≤500 cells per cm²; with adherent cells)
1. Plate cells at sufficiently low density to permit sister-sister verification based on isolated spatial relationship.
2. Allow 2-5 hours of culture time for full cell adherence,
3. Refresh medium to remove unattached cells or to make changes in culture conditions.
4. Continue culturing for 16-24 hours to allow production of sister-pairs. Culture longer to produce micro-colonies composed of TSSCs and accumulating non-stem, differentiating progeny cells.
5. Perform indirect in situ immumofluorescence (ISIF) with specific antibodies for cyclin A, cyclin D1, or cyclin A and cyclin D1 simultaneously with independent and distinctive secondary antibodies. Evaluate and quantify by standard microscopy techniques (e.g., epifluorescence microscopy, confocal microscopy).

High cell density (>500 cells per cm²) CCSP-Cyto D (with adherent or suspension cells)
1. Plate or seed cells at desired density.
2. Allow 2-5 hours for culture acclimation.
3. Refresh medium to remove unattached cells from adherent cultures or to make changes in culture conditions.
4. Treat cells with cytochalasin D for ~16 hours to induce binucleated cell formation.
5. Perform indirect ISIF with specific antibodies for cyclin A, cyclin D1, or cyclin A and cyclin D1 simultaneously with independent, distinctive secondary antibodies. Evaluate and quantify by standard microscopic techniques (e.g., epifluorescence microscopy, confocal microscopy), flow cytometry, fluorescent-activated cell sorting, or by ImageStream analysis.

We used the cell cycle phase-specific protein cyclin A as a cycling cell marker. Cyclin A is a well-described marker of cycling cells that increases progressively in level from late G1 phase to G2 phase of the cell cycle (Darzynkiewicz, Z., 1996, Cytometry 25:1-13) The inverted epifluorescence micrographs in FIG. 1 show how indirect ISIF can be employed in SP and CD assays to distinguish asymmetrically self-renewing cells (Ind-8 and HFSC) from symmetrically renewing ones (Con-3). Under conditions that foster symmetric self-renewal, sister cell pairs and CD-arrested binucleated cells show a high frequency of symmetric cyclin A detection. In contrast, under conditions that foster asymmetric self-renewal, an asymmetric pattern of cyclin A expression is significantly more frequent. The cyclin A-negative cell in asymmetrically self-renewing cell pairs is arrested at G1/S as indicated by its expression of cyclin D1 ((Darzynkiewicz, Z, supra) (data not shown).

FIG. 1 shows the initial demonstration of CCSP-SPA and CCSP-Cyto D assays using engineered cell lines that undergo TSSC symmetric or asymmetric self-renewal under experimental control (Merok et al., 2002; Rambhatla et al., 2005). Shown are inverted fluorescent micrographs from parallel CCSP-SPA (SP) and CCSP-Cyto D (CD) analyses. SYM, symmetric self-renewal. ASYM, asymmetric self-renewal. DAPI, nuclear DNA fluorescence. CyA, indirect ISIF with specific antibodies for cyclin A, an indicator for cycling late G1, S, and G2 cells with greatest expression in G2 phase. CyE, indirect ISIF with antibodies for cyclin E, an indicator for cycling late G1 and S phase cells, with highest expression in early S phase (Darzynkiewicz et al., 1996). ISIF was performed simultaneously for both CyA and CyE. CyA and CyE antibodies were of different species origin. Species-specific secondary antibodies conjugated to distinctly colored fluorochromes were used for protein-specific delineation. The colors were converted to a gray scale.

Figure 2:
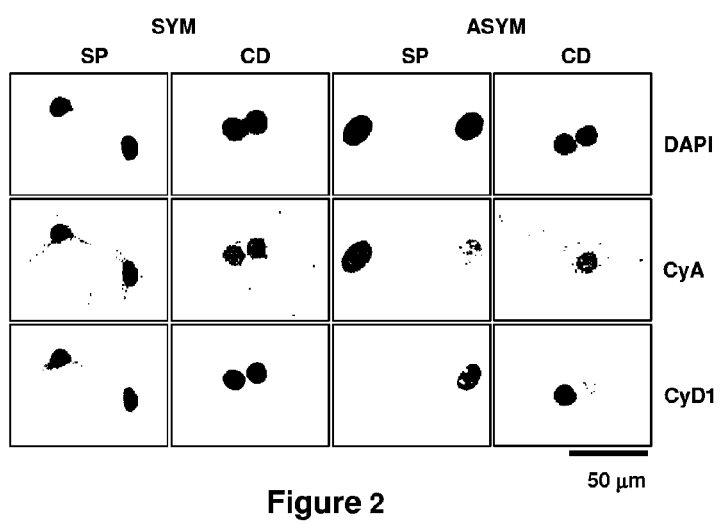
FIG. 2 shows the final demonstration of CCSP-SPA and CCSP-Cyto D assays using engineered cell lines that undergo TSSC symmetric or asymmetric self-renewal under experimental control. The inverted fluorescence images are shown. Cyclin A and cyclin D1 are CCSPs.

FIG. 2 shows a representative final demonstration of CCSP-SPA and CCSP-Cyto D assays using engineered cell lines that undergo TSSC symmetric or asymmetric self-renewal under experimental control (Merok et al., 2002; Rambhatla et al., 2005). Shown are fluorescent micrographs from parallel CCSP-SPA (SP) and CCSP-Cyto D (CD) analyses. SYM, symmetric self-renewal. ASYM, asymmetric self-renewal. DAPI, nuclear DNA fluorescence. CyA, indirect ISIF with specific antibodies for cyclin A, an indicator for cycling late G1, S, and G2 cells with greatest expression in G2 phase. CyD1, indirect ISIF with antibodies for cyclin D, an indicator for cycling or arrested late G1 and early S phase cells, with highest expression in late G1 phase (Darzynkiewicz et al., 1996). ISIF was performed simultaneously for both CyA and CyD1. CyA and CyD1 antibodies were of different species origin. Species-specific secondary antibodies conjugated to distinctly colored fluorochromes were used for protein-specific delineation. The colors were converted to a gray scale.

Test quality: The difference in the occurrences of the SYM and ASYM CyA:CyD1 patterns for the symmetric self-renewal and asymmetric self-renewal states was highly significant. P<0.0002 and p<0.0001 for CCSP-SPA and CCSP-Cyto D patterns, respectively (Fisher's exact test). Assuming that the asymmetric self-renewal rate of the engineered cell lines under SYM conditions is 0% and under ASYM conditions is 100%, the following test quality values are estimated based on CyA:CyD1 analyses:

TABLE 1

Test Quality Metrics for Assay 1: CCSP-SPA and CCSP-Cyto D for CyA:CyD1

| Assay | Sensitivity (%) | Specificity (%) Positive | Predictive Value (%) |
|---|---|---|---|
| CCSP-SPA | 44 | 94 | 88 |
| CCSP-Cyto D | 43 | 97 | 94 |

The lower sensitivity values most likely reflect over estimation of the ASYM rate. Time-lapse studies suggest that it may be as low as 85% (Rambhatla et al., 2001) which would increase the estimated sensitivity of the test.

Example 2

Assay 2

Detection of Asymmetrically Self-Renewing TSSCs with Newly Defined Asymmetric ASRA Proteins: CXCR-6, BTG2, LGR5, H2A.Z (aka H2.AZ)

Cxcr-6 (chemokine [C—X—C motif] receptor 6) and btg2 (anti-proliferative B-cell translocation gene 2) were identified as genes with highly expressed mRNAs in the ASYM state of engineered cell lines compared to the SYM state, and H2A.Z (histone 2A member Z) was identified as a gene with low mRNA expression in the ASYM state compared to the SYM state. Assay 2 is performed in the same manner as Assay 1, but makes use of commercially available antibodies specific for these ASRA proteins (i.e., "ASRA-SPA" and "ASRA-Cyto D," respectively)

Figure 3:
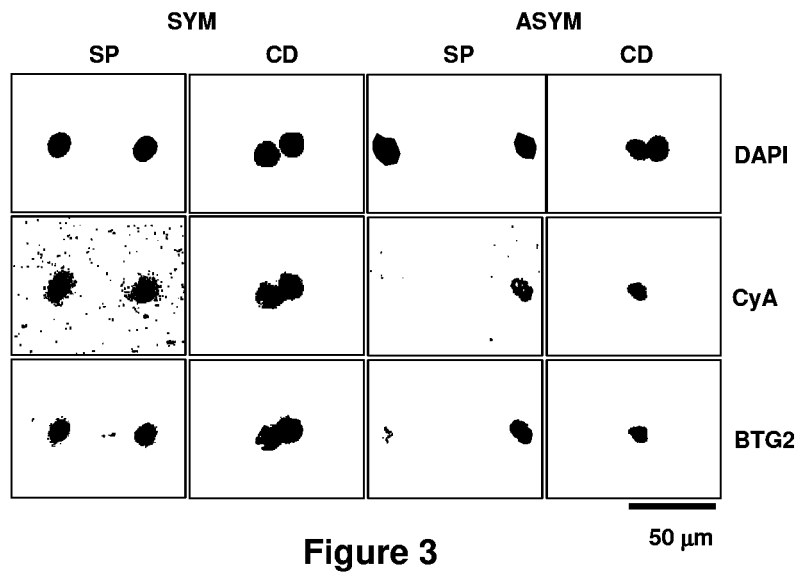
FIG. 3 shows the demonstration of ASRA-SPA and ASRA-Cyto D assays for ASRA protein BTG2 using engineered cell lines that undergo TSSC symmetric or asymmetric self-renewal under experimental control. The inverted fluorescence images are shown.

FIG. 3 is a representative demonstration of ASRA-SPA and ASRA-Cyto D assays for the ASRA protein BTG2 using engineered cell lines that undergo TSSC symmetric or asymmetric self-renewal under experimental control (Merok et al., 2002; Rambhatla et al., 2005). Shown are inverted fluorescent micrographs from parallel ASRA-SPA (SP) and ASRA-Cyto D (CD) analyses. SYM, symmetric self-renewal. ASYM, asymmetric self-renewal. DAPI, nuclear DNA fluorescence. CyA, indirect ISIF with specific antibodies for cyclin A, an indicator for cycling late G1, S, and G2 cells with greatest expression in G2 phase (Darzynkiewicz et al., 1996). BTG2, indirect ISIF with antibodies for BTG2, an ASRA protein whose mRNA is up-regulated in the ASYM state compared to the SYM state. ISIF was performed simultaneously for both CyA and BTG2. CyA and BTG2 antibodies were of different species origin. Species-specific secondary antibodies conjugated to distinctly colored fluorochromes were used for protein-specific delineation. The colors were converted to a gray scale. Note that in the ASYM state, BTG2 is expressed in the cycling cell, which models asymmetrically self-renewing TSSCs.

Test quality: SPA and Cyto D assays with CyA and BTG antibodies provide higher quality tests for TSSCs. The difference in the occurrences of the SYM and ASYM CyA:BTG2 patterns for the symmetric self-renewal and asymmetric self-renewal states was also more significant than for CyA:CyD1 tests. $P<10^{-6}$ for both ASRA-SPA and ASRA-Cyto D patterns (Fisher's exact test). Assuming that the asymmetric self-renewal rate of the engineered cell lines under SYM conditions is 0% and under ASYM conditions is 100%, the following test quality values are estimated based on CyA:BTG2 analyses:

TABLE 2

Test Quality Metrics for Assay 2: ASRA-SPA and ASRA-Cyto D for CyA:BTG2

| Assay | Sensitivity (%) | Specificity (%) Positive | Predictive Value (%) |
|---|---|---|---|
| ASRA-SPA | 58 | 93 | 90 |
| ASRA-Cyto D | 64 | 93 | 88 |

The lower sensitivity values most likely reflect over estimation of the ASYM rate. Time-lapse studies suggest that it may be as low as 85% (Rambhatla et al., 2001) which would increase the estimated sensitivity of the test.

Figure 4:
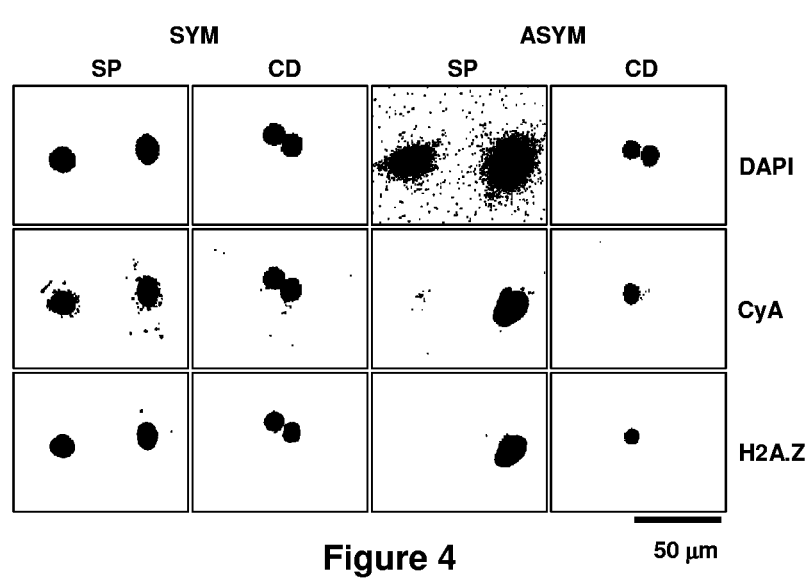
FIG. 4 shows the demonstration of ASRA-SPA and ASRA-Cyto D assays for ASRA protein H2A.Z using engineered cell lines that undergo TSSC symmetric or asymmetric self-renewal under experimental control. The inverted fluorescence images are shown.

FIG. 4 is a representative demonstration of ASRA-SPA and ASRA-Cyto D assays for the ASRA protein H2A.Z using engineered cell lines that undergo TSSC symmetric or asymmetric self-renewal under experimental control (Merok et al., 2002; Rambhatla et al., 2005). Shown are fluorescent micrographs from parallel ASRA-SPA (SP) and ASRA-Cyto D (CD) analyses. SYM, symmetric self-renewal. ASYM, asymmetric self-renewal. DAPI, nuclear DNA fluorescence. CyA, indirect ISIF with specific antibodies for cyclin A, an indicator for cycling late G1, S, and G2 cells with greatest expression in G2 phase (Darzynkiewicz et al., 1996). H2A.Z, indirect ISIF with antibodies for H2A.Z, an ASRA protein whose mRNA is down-regulated in the ASYM state compared to the SYM state. ISIF was performed simultaneously for both CyA and H2A.Z. CyA and H2A.Z antibodies were of different species origin. Species-specific secondary antibodies conjugated to distinctly colored fluorochromes were used for protein-specific delineation. The colors were converted to a gray scale. Note that in the ASYM state, H2A.Z is expressed in the cycling cell, which models asymmetrically self-renewing TSSCs. This cell is also predicted to contain the immortal DNA strands.

Test quality: SPA and Cyto D assays with H2A.Z provide higher quality tests for TSSCs. The difference in the occurrences of the SYM and ASYM CyA:H2A.Z patterns for the symmetric self-renewal and asymmetric self-renewal states was also more significant than for CyA:CyD1 tests. $P<10^{-6}$ for both ASRA-SPA and ASRA-Cyto D patterns (Fisher's exact test). Assuming that the asymmetric self-renewal rate of the engineered cell lines under SYM conditions is 0% and under ASYM conditions is 100%, the following test quality values are estimated based on CyA:BTG2 analyses:

TABLE 3

Test Quality Metrics for Assay 2: ASRA-SPA and ASRA-Cyto D with CyA:H2A.Z

| Assay | Sensitivity (%) | Specificity (%) Positive | Predictive Value (%) |
|---|---|---|---|
| ASRA-SPA | 69 | 93 | 89 |
| ASRA-Cyto D | 53 | 95 | 92 |

The lower sensitivity values most likely reflect over estimation of the ASYM rate. Time-lapse studies suggest that ASYM may be as low as 85% (Rambhatla et al., 2001) which would increase the estimated sensitivity of the test.

To certify that the method can detect bone fide TSSCs by virtue of their asymmetric self-renewal, a recently validated protein biomarker for exclusive identification of TSSCs found in murine intestinal epithelia and hair follicles was employed.

Lgr5 is leucine-rich-repeat containing G-protein-coupled receptor 5 and is also known as Gpr49. Lrg5 is a mouse gene whose mRNA expression was found to be restricted to cells in the stem cell niche regions of intestinal crypts and colonic pits. The stem cell association of Lgr5 gene expression was first established by transgenic knock-in of fluorescent protein genes into the Lgr5 expression locus (Barker et al., 2009). Commercially available anti-human LGR5 protein antibodies have also been used to identify rare positive cells in stem cell niche regions of human intestinal crypts and colonic pits (Becker et al., 2008) and it has also been shown to be expressed by mouse hair follicle stem cells (Jaks et al., 2008). The functional validation of LGR5-expressing cells is ongoing, but these reports establish LGR5 protein as a highly specific biomarker for TSSCs in intestinal epithelia and hair follicles.

LGR5 ISIF analyses were used to evaluate independently the TSSC-phenotype of engineered cell lines and clonal, SACK-expanded mouse hair follicle stem cells (Strains 3C5 and 5B8 described in U.S. Pat. No. 7,655,465). Both the engineered cell lines and SACK-expanded mouse hair follicle stem cell strains express LGR5 abundantly, indicating TSSC identity. Moreover, they do so asymmetrically. In the case of the engineered fibroblast cell lines, LGR5 expression is nuclear. It is expressed in the nuclei of both sisters of SYM divisions. However, in the ASYM condition, often it is only expressed in the nucleus of one sister of ASYM divisions and that sister corresponds to the CyA-expressing stem-like cell (FIG. 5).

Figure 5:
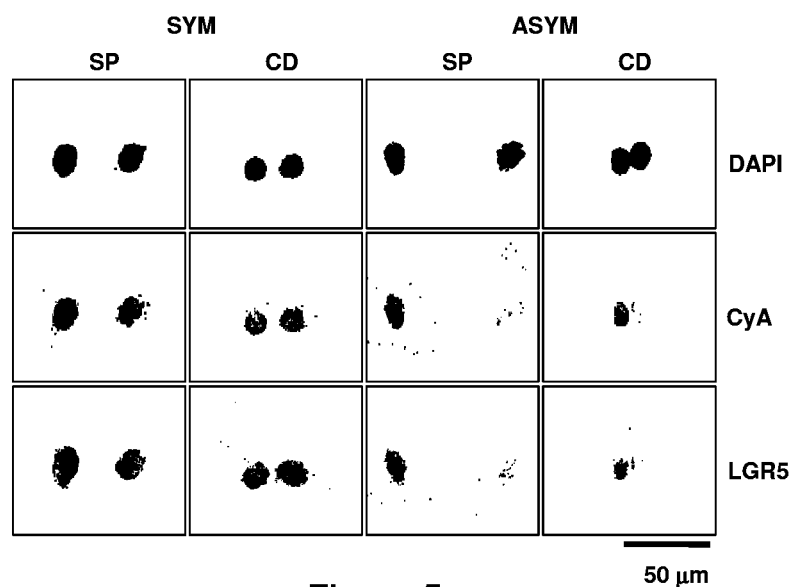
FIG. 5 shows the detection of TSSC biomarker LGR5 expression in SPA and Cyto D assays with engineered fibroblast cell lines that undergo TSSC symmetric or asymmetric self-renewal under experimental control.

FIG. 5 is a representative demonstration of the detection of TSSC biomarker LGR5 expression in SPA and Cyto D assays with engineered fibroblast cell lines that undergo TSSC symmetric or asymmetric self-renewal under experimental control (Merok et al., 2002; Rambhatla et al., 2005). Shown are fluorescent micrographs from parallel SPA (SP) and Cyto D (CD) analyses. SYM, symmetric self-renewal. ASYM, asymmetric self-renewal. DAPI, nuclear DNA fluorescence. CyA, indirect ISIF with specific antibodies for cyclin A, an indicator for cycling late G1, S, and G2 cells with greatest expression in G2 phase (Darzynkiewicz et al., 1996). LGR5, indirect ISIF with specific antibodies for LGR5. ISIF was performed simultaneously for both CyA and LGR5. CyA and LGR5 antibodies were of different species origin. Species-specific secondary antibodies conjugated to distinctly colored fluorochromes were used for protein-specific delineation. The colors were converted to a gray scale. Note that in the ASYM state, LGR5 is expressed in the nucleus of the cycling cell, which models asymmetrically self-renewing TSSCs.

Figure 6:
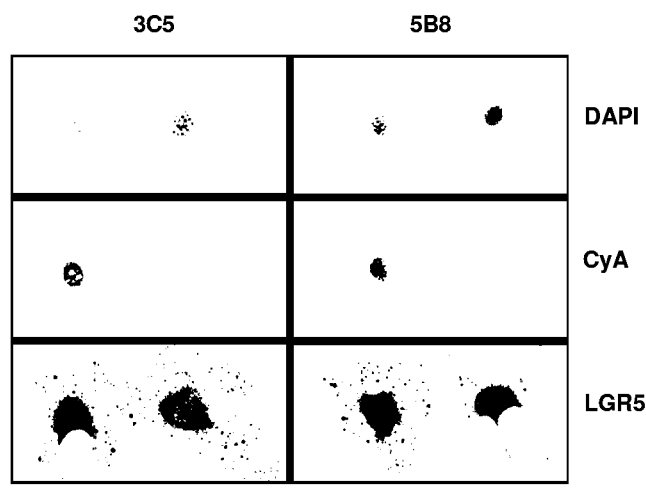
FIG. 6 shows the detection of TSSC biomarker LGR5 expression in SPA with mouse hair follicle stem cell strains 3C5 and 5B8. The inverted fluorescence images are shown.
Figure 7:
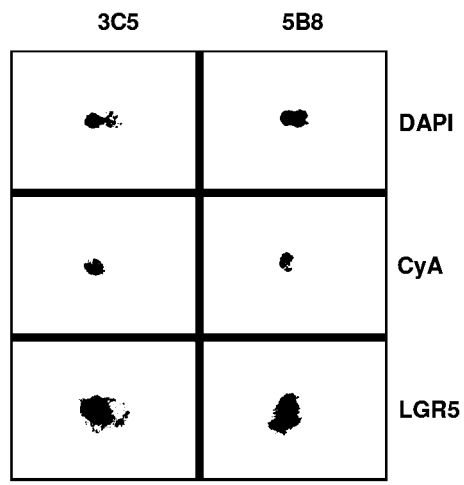
FIG. 7 shows the detection of TSSC biomarker LGR5 expression in Cyto D analyses with mouse hair follicle stem cell strains 3C5 and 5B8. The inverted fluorescence images are shown.

In SACK-expanded hair follicle stem cell strains 3C5 and 5B8, evaluated under SACK-free conditions to foster ASYM divisions, LGR5 expression is detected in both the cytoplasm and the nucleus. Importantly, the nuclear expression is often asymmetric between sister cells, and specifically associated with the CyA-expressing cycling stem cell (FIGS. 6 and 7). In CyA:LGR5 Cyto D analyses (FIG. 7), 39-51% of binucleated cells show the asymmetric pattern indicative of TSSCs.

FIG. 6 shows the detection of TSSC biomarker LGR5 expression in SPA with mouse hair follicle stem cell strains 3C5 and 5B8. Shown are fluorescent micrographs from SPA analyses with the indicated biomarkers. DAPI, nuclear DNA fluorescence. CyA, indirect ISIF with specific antibodies for cyclin A, an indicator for cycling late G1, S, and G2 cells with greatest expression in G2 phase (Darzynkiewicz et al., 1996). LGR5, indirect ISIF with specific antibodies for LGR5. ISIF was performed simultaneously for both CyA and LGR5. CyA and LGR5 antibodies were of different species origin. Species-specific secondary antibodies conjugated to distinctly colored fluorochromes were used for protein-specific delineation. The colors were converted to a gray scale. Note that LGR5 is expressed in the nuclei of the cycling cells that correspond to asymmetrically self-renewing hair follicle stem cells, but not expressed at similar levels in the nuclei of arrested non-stem cell sister cells.

FIG. 7 shows the detection of TSSC biomarker LGR5 expression in Cyto D analyses with mouse hair follicle stem cell strains 3C5 and 5B8. Shown are fluorescent micrographs from Cyto D analyses with the indicated biomarkers. DAPI, nuclear DNA fluorescence. CyA, indirect ISIF with specific antibodies for cyclin A, an indicator for cycling late G1, S, and G2 cells with greatest expression in G2 phase (Darzynkiewicz et al., 1996). LGR5, indirect ISIF with specific antibodies for LGR5. ISIF was performed simultaneously for both CyA and LGR5. CyA and LGR5 antibodies were of different species origin. Species-specific secondary antibodies conjugated to distinctly colored fluorochromes were used for protein-specific delineation. The colors were converted to a gray scale.

It is noteworthy that asymmetrically self-renewing 3C5 HFSCs also show asymmetric nuclear detection of LGR5, which is highly correlated with cyclin A nuclear detection. In sister pairs and paired CD nuclei that display symmetric cyclin A detection, LGR5 detection is also symmetric (data not shown). In CD analyses with xanthine supplementation to suppress asymmetric self-renewal, 25±8% (n=3; examined binucleated cells range=55-64) of 3C5 divisions show asymmetric co-detection of cyclin A and LGR5. In contrast, in xanthine-free medium, the frequency of divisions with asymmetric co-detection increases to 53±12% (n=3; examined binucleated cells range=59-66). This highly significant difference in self-renewal pattern (p<0.0004; Fisher's exact test) is consistent with LGR5 marking HFSCs that shift between symmetric self-renewal and asymmetric self-renewal in response to the SACK agent xanthine. The cells produced by asymmetric divisions that are negative for both cyclin A and LGR5 are consistent with differentiating non-stem cells.

These data provide an orthogonal demonstration that the SPA and Cyto-D methods for detection of asymmetrically self-renewing cells provide detection and quantification of TSSCs. Moreover, since asymmetric self-renewal is a universal property of TSSCs, these methods can be used to identify and quantify TSSCs even if they do not express LGR5.

Example 3

Assay 3

Detection of Immortal DNA Strands in Mitotic TSSCs

H2A.Z is a histone 2A variant that is highly represented in nucleosomes found at kinetochore associated DNA. The detection of a protein of this property only in the nucleus of the cycling stem cell sister of asymmetric self-renewal divisions might reflect a specific association of H2A.Z with the chromosomes bearing immortal DNA strands, which also reside in the cycling stem cell sister. The predicted down-regulation of the protein could create a state that fosters asymmetric localization of limiting H2A.Z protein to immortal DNA strand-containing chromosomes at the expense of binding to chromosomes containing only mortal DNA strands. The inverted fluorescence micrographs shown in FIG. 8 demonstrate this prediction and thereby embody the instant invention for universal detection of TSSCs.

Figure 8:
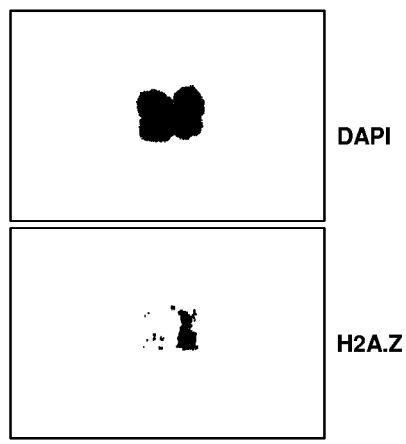
FIG. 8 shows the demonstration that H2A.Z protein is asymmetrically detected on the metaphase chromosomes of cells undergoing immortal DNA strand co-segregation (IDSC). The inverted fluorescence images are shown.

FIG. 8 is a representative demonstration that H2A.Z protein is asymmetrically detected on the metaphase chromosomes of cells undergoing immortal DNA strand co-segregation (IDSC). Shown is a fluorescence micrograph of a metaphase mitotic cell found in a culture of engineered fibroblasts under conditions for asymmetric self-renewal and associated IDSC (Merok et al., 2002; Rambhatla et al., 2005). DAPI, chromosomal DNA fluorescence. H2A.Z, indirect ISIF with antibodies for H2A.Z, an ASRA protein whose mRNA is down-regulated in the ASYM state compared to the SYM state.

In SP and CD analyses with the engineered cells Ind-8, H2A.Z nuclear detection was highly associated with cyclin A nuclear detection, including both symmetrically self-renewing and asymmetrically self-renewing patterns (FIG. 4, compare CyA to H2A.Z). In $ZnCl_2$-supplemented medium, which induces asymmetric self-renewal and immortal DNA strand co-segregation in Ind-8 cells, 56±13% (n=3; examined pairs range=60-72) and 45±8% (n=3; examined pairs range=60-69) of Ind-8 cell divisions showed asymmetric co-detection of cyclin A and H2A.Z in SP and CD analyses, respectively. However, Con-3 cells, grown under the same conditions, yielded only 9±5% (n=3; examined pairs range=61-74) and 8±4% (n=3; examined pairs range=63-73) divisions with asymmetric co-detection, respectively. The greatly reduced frequency ($p<10-6$; Fisher's exact test) confirmed that asymmetric co-detection of H2A.Z with cyclin A was specific for asymmetric self-renewal.

Figure 9:
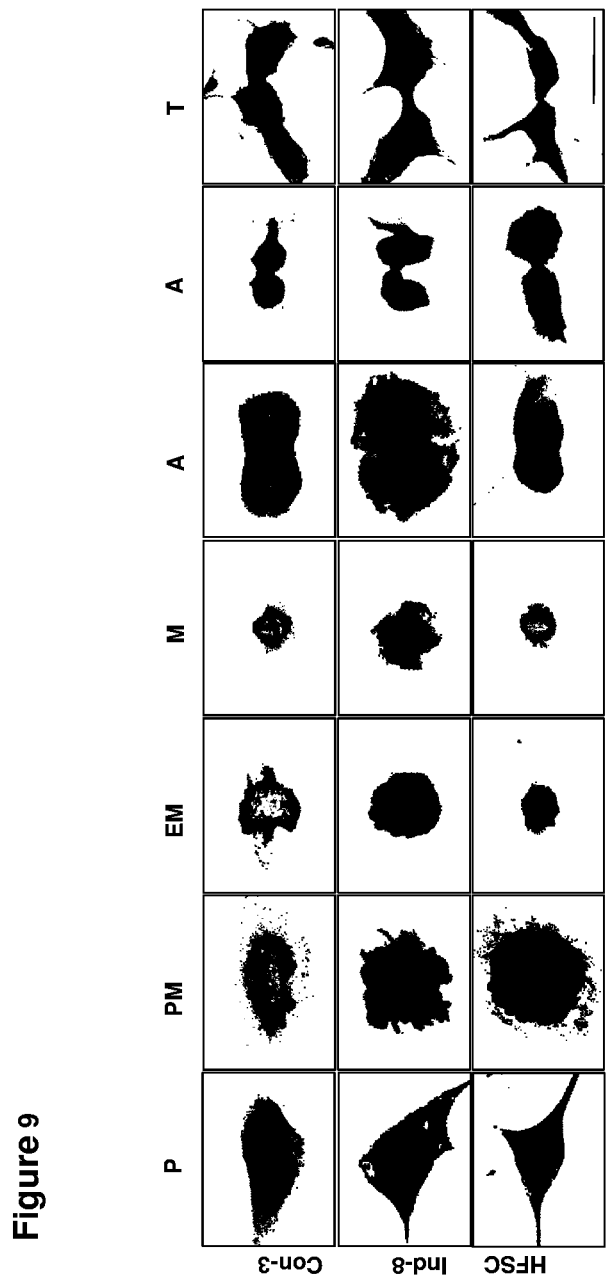
FIG. 9 shows that H2A.Z detection is asymmetrically associated with segregating sets of chromosomes in asymmetric self-renewing mitotic cells. P, prophase; PM, prometaphase; EM, early metaphase; M, late metaphase; A, anaphase; and T, telophase of mitosis. The inverted fluorescence images are shown. Scale bar=25 μm.

Given the previously described tight association between asymmetric self-renewal and immortal DNA strand co-segregation (Rambhatla et al., 2005), we considered that, since it was an intrinsic nucleosome protein, the interphase detection pattern of H2A.Z can be a continuation of its chromosomal detection pattern in the preceding mitosis. Consistent with this expectation, Con-3 cells, which exhibited a high fraction of symmetric co-detection of nuclear H2A.Z and cyclin A in SP and CD analyses (~89%) showed a high fraction of mitoses with uniform detection of H2A.Z on both segregating complements of mitotic chromosomes (FIG. 9, Con-3; 82±4%; n=3; examined mitoses range=49-63). Ind-8 cells, grown under conditions for asymmetric self-renewal and immortal DNA strand co-segregation, showed a markedly different pattern of chromosomal H2A.Z detection. Forty-two ±13% of Ind-8 mitoses (n=3; examined mitoses range=47-59; $p<10-6$, Fisher's exact test) showed H2A.Z on only one complement of segregating chromosomes (FIG. 9, Ind-8).

Asymmetric detection of mitotic chromosome H2A.Z was not limited to the engineered cell lines. Assay 3 is performed in the same manner as Assay 2 using commercially available antibodies specific for H2A.Z, except either naturally occurring mitotic cells (prophase, metaphase, anaphase, and telophase stages) or cells arrested with mitotic arrest agents (e.g., 0.1 µM colcemid) are evaluated. FIG. 9 are examples of merged inverted for DAPI, to detect chromosomal DNA (darker gray areas); indirect ISIF for α-tubulin to identify the mitotic spindle (black area), and indirect ISIF for H2A.Z (very light gray areas). Con-3, mitotic p53-null cells undergoing symmetric self-renewal; Ind-8, mitotic p53-expressing cells undergoing asymmetric self-renewal; and HFSC, mitotic 3C5 hair follicle stem cells under conditions that promote asymmetric self-renewal. In xanthine-free conditions, which promote their asymmetric self-renewal, 34±8% (n=3; examined mitoses range=59-66) of 3C5 HFSCs also displayed H2A.Z detection limited only to one set of segregating chromosomes (FIG. 9, HFSC). This H2A.Z detection pattern was associated with asymmetric self-renewal, as growth of 3C5 cells under SACK conditions with xanthine-supplementation reduced the frequency of asymmetric H2A.Z detection to 11±3% (n=3; examined mitoses range=55-64; p<0.0025, Fisher's exact test).

When chromosomal H2A.Z detection was asymmetric, it also differed in quality. In symmetric mitoses, H2A.Z immunofluorescence was granular and distributed in close correspondence with fluorescence due to DNA (FIG. 9, Con-3). However, when asymmetrically detected, H2A.Z immunofluorescence was more uniform and compact; and coincident with only a sub-fraction of the area of chromosomal DNA fluorescence (FIG. 9, Ind-8 and HFSC). This "clustering" of H2A.Z immunofluorescence was evident even in prophase cells (FIG. 9, Ind-8 and HFSC, P).

Figure 10:
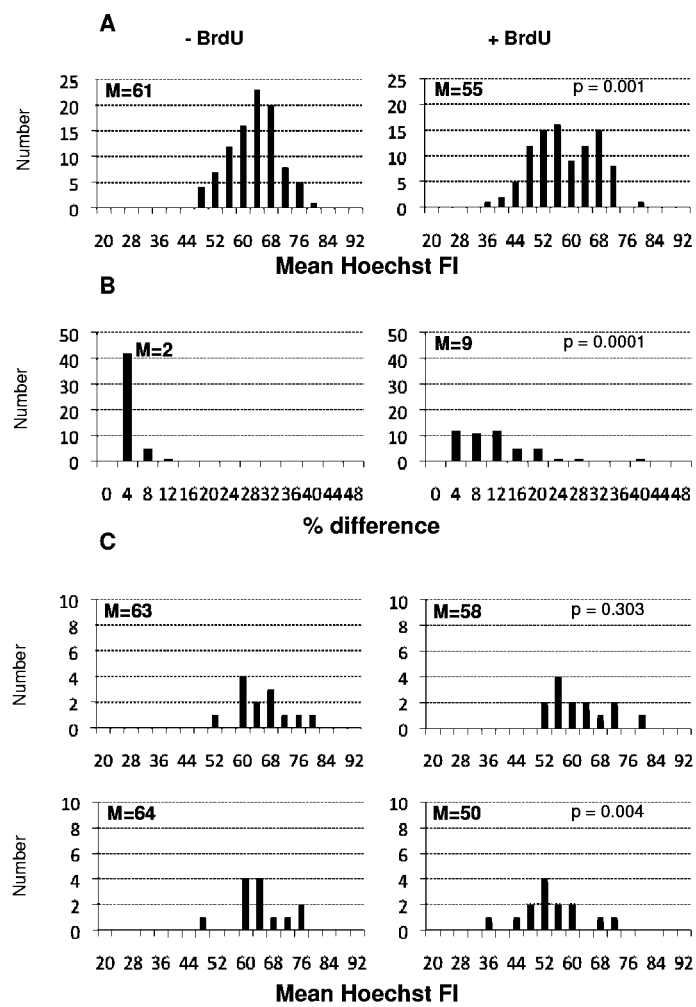
FIG. 10A shows the distribution of the mean Hoechst fluorescence intensity (FI) for independent segregating sets of chromosomes in late metaphase and anaphase cells undergoing immortal DNA strand co-segregation without or with pulse-chase labeling with BrdU, independent of their H2A.Z detection pattern.
FIG. 10B shows the distribution of the percent differences in Hoechst FI between paired segregating sets of chromosomes in individual late metaphase and anaphase cells.
FIG. 10C shows the distribution of the mean Hoechst FI for individual segregating sets of chromosomes identified by indirect ISIF in H2A.Z asymmetric mitoses as either H2A.Z-negative (top graphs) or H2A.Z-positive (bottom graphs). M, distribution median; p, Kolmogrov-Smirnoff test confidence level that the respective left-right paired distributions are not equivalent.

Because it is known that the newly divided cycling sister cell of TSSC asymmetric self-renewal divisions inherits the immortal DNA strands and becomes the sister with the H2A.Z-positive nuclear DNA in interphase, it can be concluded that chromosomes bearing immortal DNA strands are marked by H2A.Z detection. We employed a label-retention procedure (Merok et al., 2002 and Rambhatla et al., 2005) to confirm this inference. Ind-8 cells were labeled with BrdU for one generation period under conditions for symmetric self-renewal and random chromosome segregation. Asymmetrically detected H2A.Z co-distributes with immortal DNA strands in asymmetrically self-renewing mitotic cells. Ind-8 cells were grown under conditions for random chromosome segregation in either BrdU-free medium (FIG. 10A, −BrdU, left graphs) or medium supplemented with BrdU (FIG. 10A, +BrdU, right graphs). After 24 hours, both types of cultures were shifted to BrdU-free medium with $ZnCl_2$ to induce asymmetric self-renewal and immortal DNA strand co-segregation and then cultured for an additional 96 hours (~4 generation periods). Cells were fixed for H2A.Z indirect ISIF and stained with Hoechst dye as an indicator of BrdU content. In this scheme, immortal DNA strands are identified as BrdU-labeled DNA strands that persist in cycling cells as complete genomic complements of hemi-substituted chromosomes.

Detection of H2A.Z proved incompatible with detection of BrdU by indirect ISIF. Therefore, we used the ability of BrdU to quench the fluorescence of DNA-bound Hoechst dyes to detect and quantify BrdU-labeled immortal DNA strands simultaneously with H2A.Z (Merok et al., 2002 and Rambhatla et al., 2005). At the end of the 96-hour BrdU-free culture period, we performed indirect ISIF for H2A.Z detection and counter-stained with Hoechst dye instead of DAPI. Segregating complements of chromosomes in late metaphase and anaphase cells were imaged and quantified for mean Hoechst fluorescence intensity.

FIG. 10A (left) shows the uniform mean intensity distribution of unquenched Hoechst fluorescence for total segregating chromosome sets, independent of H2A.Z detection pattern, from control Ind-8 cells maintained in BrdU-free medium at all times. In contrast, Ind-8 cells that received the initial 24-hour period of BrdU-labeling showed a significant bimodal mean fluorescence intensity distribution (FIG. 10A, right). The two histogram peaks correspond to bright unquenched chromosome sets and dim quenched sets, the latter retaining hemi-substituted BrdU for ~4 generation periods of cell division. To demonstrate that unquenched and quenched sets of chromosomes occurred in the same mitotic cells, we determined the differences in the mean fluorescence intensity between chromosome complements in individual cells. As shown in FIG. 10B, compared to unlabeled cells (left), segregating chromosome sets in pulse-labeled cells (right) had a significantly larger median difference, consistent with the expectation for immortal DNA strand co-segregation.

Next, we assessed how asymmetrically detected H2A.Z related to the immortal DNA strand content of segregating chromosomes. As revealed in FIG. 10C (top right), H2A.Z-negative chromosome sets had a bright, unquenched, Hoechst fluorescence distribution that was similar to the distribution for H2A.Z-negative chromosomes in unlabeled control cells (FIG. 10C, top left). In contrast, H2A.Z-positive chromosome sets had a dim, quenched distribution, indicative of immortal DNA strands (FIG. 10C, bottom right). Their distribution was significantly distinct from the distributions of either the H2A.Z-positive chromosomes of unlabeled cells (FIG. 10C, bottom left) or the H2A.Z-negative chromosomes of labeled cells (FIG. 10C, top right; p=0.039).

Example 4

Demonstration of H2A.Z Mitotic Asymmetry In Vivo

Figure 11:
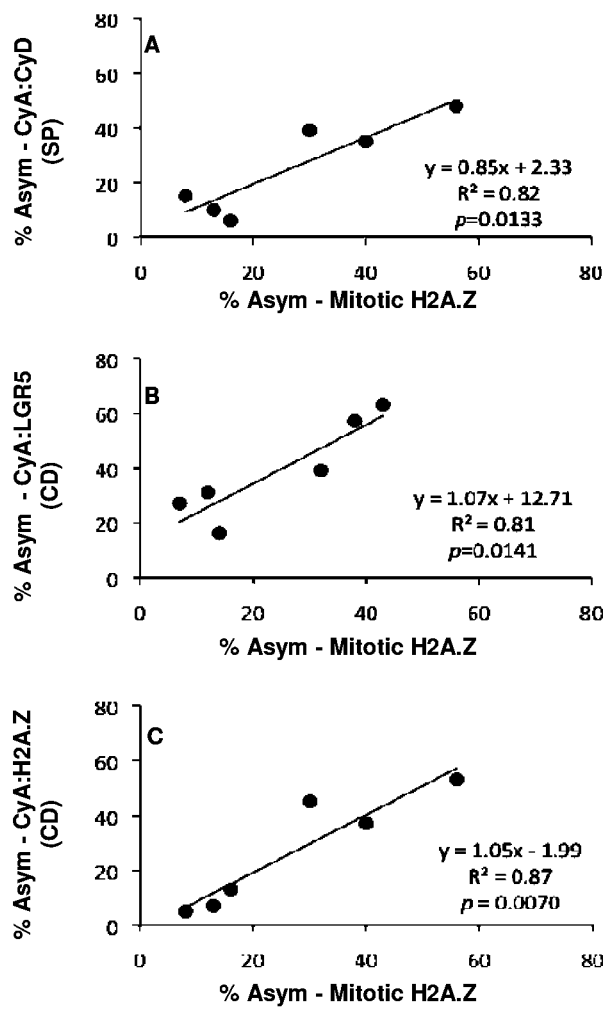
FIG. 11A shows linear regression analyses of engineered cell lines that undergo TSSC symmetric or asymmetric self-renewal under experimental control. % Asymmetric self-renewal determinations were based on indirect ISIF detection patterns of cyclin A (CyA, as in FIG. 4) and cyclin D (CyD; Huh and Sherley, unpublished) in SP analyses. Each data point corresponds to an independent analysis under identical conditions that either limited or promoted asymmetric self-renewal of the indicated cells.
FIG. 11B shows linear regression analyses of SACK-expanded HFSC strain 3C5. % Asymmetric self-renewal was based on indirect ISIF detection patterns of cyclin A and LGR5 in CD analyses (as in FIG. 4). Each data point corresponds to an independent analysis under identical conditions that either limited or promoted asymmetric self-renewal of the indicated cells.
FIG. 11C shows linear regression SP analyses of engineered Con-3 and Ind-8 cells. % Asymmetric self-renewal determinations were based on indirect ISIF detection of cyclin A and H2A.Z (as in FIG. 4). Each data point corresponds to an independent analysis under identical conditions that either limited or promoted asymmetric self-renewal of the indicated cells.

Asymmetric mitotic H2A.Z on mitotic chromosomes is highly associated with asymmetric self-renewal. This essential co-dependency has been overlooked in studies that fail to detect immortal DNA strand co-segregation (Kiel et al., 2007; Sotiropoulou et al., 2008; and Waghmare et al., 2008). Our findings illustrate further the implicit tight connection between immortal DNA strand co-segregation and asymmetric self-renewal envisioned by Cairns. (Cairns, 1975; Merok et al., 2002 and Rambhatla et al., 2005). Linear regression analyses were performed to quantify associations between asymmetric self-renewal, indicated by % asymmetric sister cell pairs (SP) or % asymmetric sister nuclei after cytochalasin D (CD) treatment (respective y-axes), and % asymmetric H2A.Z detection on mitotic chromosomes α-axes). As shown in FIGS. 11A and 11B, both the engineered cells and the HFSCs, respectively, show a significant association between frequencies of asymmetric self-renewal and frequencies of immortal DNA strand co-segregation defined by asymmetric detection of chromosomal H2A.Z in mitotic cells. A similarly significant association occurs with asymmetric self-renewal determined by CD analyses employing co-detection of cyclin A and H2A.Z (FIG. 11C). This association is consistent with our initial idea that H2A.Z-positive mitotic chromosome sets maintain their distinctive H2A.Z-positive character into the subsequent stem cell interphase. These unique "pattern-specific biomarkers" set the stage for routine identification of rare cells that co-segregate immortal DNA strands in tissues, i.e., DSCs.

As a first test of this concept, we looked for cells with H2A.Z asymmetry in pre-crisis mouse embryo fibroblast cultures and in tissue sections containing hair follicles of adult mouse skin. To accomplish these studies, we optimized the in vitro indirect ISIF mitotic cell assays for use in tissue sections. In particular, we paired the mitosis-specific biomarker phosphorylated histone H3 (pH3) with H2A.Z to develop a highly sensitive assay for detecting rare tissue cells with mitotic chromosome H2A.Z asymmetry, by focusing the analysis to mitotic cells. The early passage pre-crisis cultures are closer in cell make-up to primary dissociated tissue cell preparations than are immortalized cell lines. For use with tissue sections, the in vitro indirect ISIF mitotic cell assay for H2A.Z required refinement. This was because α-tubulin is not sufficiently specific to detect only mitotic cells in tissues, because non-mitotic cells have a wide range of α-tubulin expression and polymerization.

Figure 14:
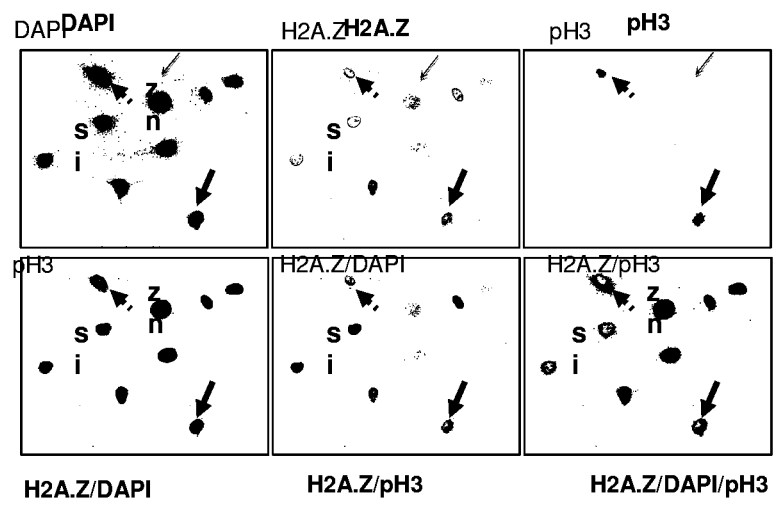
FIG. 14 shows the symmetric H2A.Z localization in prophase nuclei detected by phosphorylated histone H3 in cultures of pre-crises mouse embryonic fibroblasts. DAPI, nuclear DNA fluorescence. H2A.Z, indirect ISIF with antibodies for H2A.Z. pH3, indirect ISIF with specific antibodies for phosphorylated histone H3. The inverted fluorescence images are shown.

FIG. 12 shows examples of this assay when applied to cultured cells. SYM, Example of Con-3 p53-null cell undergoing symmetric self-renewal. ASYM, Example of Ind-8 p53-expressing cell undergoing asymmetric self-renewal. HFSC, Example of 3C5 hair follicle stem cells undergoing asymmetric self-renewal under Xn-free conditions. DAPI, nuclear DNA fluorescence. pH3, indirect ISIF with specific antibodies for phosphorylated histone H3. H2A.Z, indirect ISIF with antibodies for H2A.Z. Indirect ISIF was performed simultaneously for pH3 and H2A.Z. Merge is the result of overlaid pH3 and H2A.Z images. Ninety-three percent of symmetrically cycling pH3-positive, prophase Con-3 cells had H2A.Z immunofluorescence that was symmetrically distributed with respect to pH3 immunofluorescence. In contrast, 32% and 20% of pH3-positive prophase cells in cultures of engineered cells and HFSCs under conditions that promote asymmetric self-renewal, respectively, had a smaller, asymmetric distribution of H2A.Z immunofluorescence on the background of pH3 immunofluorescence. In preliminary analyses with cultures of early passage (17 population doublings), pre-crises mouse embryo fibroblasts, 7% of prophase cells displayed H2A.Z asymmetry. In contrast, in parallel immortalized cultures (50 population doublings), 0 out of 110 examined prophase cells showed asymmetry. Similarly, 0 out of 123 examined prophases in early passage (12 population doublings) cultures from p53 gene knockout mice showed H2A.Z asymmetry. This is a significant difference in detection ($p<0.009$); and it is consistent with our hypothesis that immortalization, which is known to be highly associated with p53 gene mutation, manifests a permanent conversion of long-lived tissue stem cells from asymmetric self-renewal to symmetric self-renewal (Lee et al., 2003; Rambhatla et al., 2001). FIG. 14 provides a view of how rare prophase cells with H2A.Z asymmetry are found among interphase cells with varying amounts of symmetric H2A.Z expression as a function of their position in the cell cycle. Indirect ISIF was performed simultaneously for pH3 and H2A.Z. Top row of FIG. 14, individual fluorescence images. Bottom row of FIG. 14, merged upper images as denoted. Solid black arrows, example of a prophase nucleus with asymmetric H2A.Z localization. Black dotted arrows, example of prophase nucleus with symmetric H2A.Z. si, example of interphase nucleus (i.e., pH3-negative) with symmetric H2A.Z localization. zn, H2A.Z-negative interphase nucleus. H2A.Z-negative interphase cells are also observed (FIG. 14, zn). Such cells are predicted to result from asymmetric self-renewal divisions by tissue stem cells in the cultures.

Figure 13A:
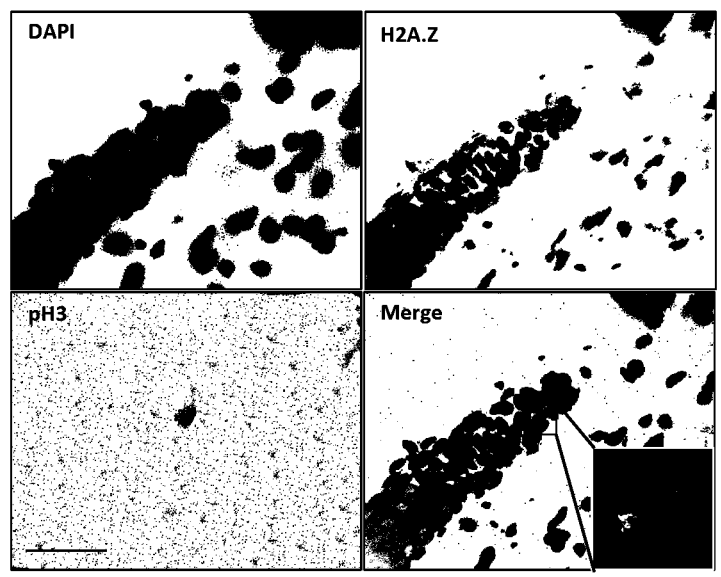
FIGS. 13A and 13B are independent sections showing the detection of mitotic cells with asymmetric H2A.Z at the base of mouse hair follicles. The inverted fluorescence images are shown. Scale bar=50 μm. Inset, 5× magnification of the mitotic cell detected with asymmetric H2A.Z. Scale bar=10 μm. Note: In section A, hair shaft emerges through lower left corner of images.
Figure 13B:
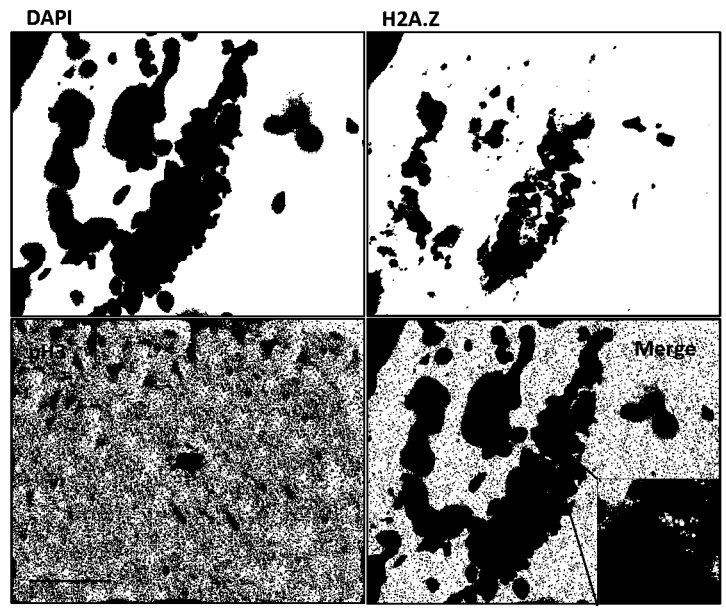

Using the new mitosis-specific assay, we evaluated 10-micron sections of adult mouse skin that contained hair follicles. Ten-micron thick, paraffin-embedded sections of adult mouse skin were evaluated by indirect ISIF with specific antibodies for H2A.Z and phosphorylated histone H3 (pH3), a biomarker for mitotic cells. DAPI was used to counter-stain nuclear and chromosomal DNA. Merge, combined indirect ISIF images for H2A.Z and pH3. Cells positive for pH3 were rare in these sections, as expected for mitotic cells. However, we found that 22% of the identified pH3-positive cells (14 of 64 detected in 183 sectioned hair follicles) showed H2A.Z asymmetry as shown in the examples given in FIGS. 13A and 13B. The mitotic cells with asymmetric H2A.Z were consistently found at the base of hair follicles, in the location where LGR5+ HFSCs have been shown to reside (Jak et al., 2008).

We have demonstrated the significance of H2A.Z mitotic asymmetry. H2A.Z mitotic asymmetry is the first distinguishing endogenous molecular feature defined for immortal DNA strands. Presently, we also consider the possibility that the apparent absence of H2A.Z in chromosomes bearing "mortal" DNA strands may be due to molecular occlusion. However, experiments performed with antibodies raised against the entire H2A.Z protein give similar results (data not shown); and H2A.Z remains undetectable in de-condensed interphase chromosomes. Either the presence or absence of H2A.Z could reflect the action of molecular machines responsible for immortal DNA strand co-segregation. An attractive hypothesis is that the tight clustering of H2A.Z immunofluorescence, reminiscent of the clustering of indirect ISIF-detected BrdU-labeled immortal DNA strands (Merok et al., 2002 and Rambhatla et al., 2005) insinuates the responsible molecular mechanism.

H2A.Z mitotic asymmetry promises to be a new pattern-specific biomarker for detecting cells undergoing asymmetric self-renewal and immortal DNA strand co-segregation. To the degree that these tightly associated processes are unique to TSSCs, H2A.Z asymmetry has potential to provide a specific and universal biomarker for diverse TSSCs in mammalian tissues. The detection of rare cycling cells with H2A.Z asymmetry at the base of mouse hair follicles is a first step towards validation of this approach. LGR5+, bone fide HFSCs have been identified in the same region (Jak et al., 2008). Our demonstration that LGR5+ HFSCs (which were expanded from mouse hair follicles based on control of asymmetric self-renewal) display H2A.Z asymmetry provides evidence that the mitotic cells detected in vivo with H2A.Z symmetry are, in fact, HFSCs. Although the hair follicle is but one TSSC compartment, the fundamental importance of asymmetric self-renewal, and potentially immortal DNA strand co-segregation, for tissue cell homeostasis, make it likely that H2A.Z asymmetry will identify TSSCs in many other tissues as well.

REFERENCES

Barker, N., Ridgway, R. A, van Es, J. H., van de Wetering, M., Begthel, H., van den Born, M., Danenberg, E., Clarke, A. R., Sansom, O. J., Clevers, H. (2009) "Crypt Stem Cells As The Cells-Of-Origin Of Intestinal Cancer," Nature 457, 608-611.

Becker, L., Huang, Q., Mashimo, H. (2008) "Immunostaining Of Lgr5, An Intestinal Stem Cell Marker, In Normal And Premalignant Human Gastrointestinal Tissue," ScientificWorldJournal 8, 1168-1176.

Cairns, J. Mutation selection and the natural history of cancer. Nature 255, 197-200 (1975). Darzynkiewicz, Z., Gong, J., Ardelt, B., and Traganos, F. (1996) "Cytometry of Cyclin Proteins," Cytometry 25, 1-13.

Hoeller, D. et al. An improved and rapid method to construct skin equivalents from human hair follicles and fibroblasts. Exp. Dermatol. 10, 264-271 (2001).

Jaks, V., Barker, N., Kasper, M., van Es, J. H., Snippert, H. J., Clevers, H., and Toftgard, R. (2008) "Lgr5 Marks Cycling, Yet Long-Lived, Hair Follicle Stem Cells," Nature Gen 40, 1291-1299.

Jahoda, C. & Oliver, R. F. The growth of vibrissa dermal papilla cells in vitro. Br. J. Dermatol. 105, 623-627 (1981)

Kiel, M. J. et al. Haematopoietic stem cells do not asymmetrically segregate chromosomes or retain BrdU. Nature 449, 238-242 (2007).

Kobayashi, K., Rochat, A., & Barrandon, Y. Segregation of keratinocyte colony-forming cells in the bulge of the rat vibrissa. Proc. Natl. Acad. Sci. USA 90, 7391-7395 (1993).

Lee, H.-S., Crane, G. G., Merok, J. R., Tunstead, J. R., Hatch, N. L., Panchalingam, K., Powers, M. J., Griffith, L. G., and Sherley, J. L. (2003) "Clonal Expansion of Adult Rat Hepatic Stem Cell Lines by Suppression of Asymmetric Cell Kinetics (SACK)", Biotech. & Bioeng. 83, 760-771.

Merok, J. R., Lansita, J. A., Tunstead, J. R., and Sherley, J. L. (2002) "Co-segregation of Chromosomes Containing Immortal DNA Strands in Cells That Cycle With Asymmetric Stem Cell Kinetics," Cancer Research, 62, 6791-6795.

Oliver, R. F. Whisker growth after removal of the dermal papilla and lengths of follicle in the hooded rat. J. Embryol. Exp. Morph. 15, 331-347 (1966).

Rambhatla, L. et al. Cellular senescence: ex vivo p53-dependent asymmetric cell kinetics. J. Biomed. Biotech. 1, 27-36 (2001).

Rambhatla, L., Ram-Mohan, S., Cheng, J. J., Sherley, J. L. (2005) "Immortal DNA Strand Co-Segregation Requires p53/IMPDH-Dependent Asymmetric Self-Renewal Associated with Adult Stem Cells," Cancer Research 65, 3155-3161.

Sherley, J. L. & King, J. Methods for ex vivo propagation of somatic hair follicle stem cells. U.S. Pat. No. 7,655,465 B2, Feb. 2, 2010.

Sotiropoulou, P. A., Candi, A., Blanpain, C. The majority of multipotent epidermal stem cells do not protect their genome by asymmetrical chromosome segregation. Stem Cells 11, 2964-73 (2008).

Waghmare, S. K. et al. Quantitative proliferation dynamics and random chromosome segregation of hair follicle stem cells. EMBO J. 27, 1309-1320 (2008).

What is claimed:

1. A method for determining the percent of asymmetrically self-renewing dividing cells in a sample of cells comprising:
   a. contacting a sample of cells with an antibody against an asymmetric self-renewal-associated (ASRA) protein to form an antibody-protein complex, wherein an antibody-protein complex is formed in situ and wherein the ASRA protein is a pattern-specific asymmetrically located protein in a cell undergoing asymmetrical cell kinetics selected from the group consisting of CXCR-6, BTG2, LGR-5 and H2A.FZ;
   b. detecting sister cell pairs of dividing cells or binucleated cells;
   c. detecting the antibody-protein complexes in sister cell pairs or binucleated cells, wherein the binucleated cells are arrested in cytokinesis;
   d. counting the total number of cells in the sample;
   e. counting the number of dividing cell comprising the pattern-specific asymmetrically localized antibody-protein complex; and
   f. computing the percent of asymmetrically self-renewing dividing cells in the sample by dividing the number of step e with the number of step d.

2. A method for determining the percent of asymmetrically self-renewing dividing cells in a tissue comprising:
   a. obtaining a biological sample from the tissue;
   b. measuring the percent of asymmetrically self-renewing dividing cells in the biological ample from step (a) according to the method of claim 1.

3. The method of claim 1, wherein the sample of cells is grown and cultured in low cell density of about $1 \times 10^3$ cells/ml.

4. The method of claim 1, wherein the sample of cells are grown and cultured in high cell density of about $1 \times 10^5$ cells/ml.

5. The method of claim 1, wherein the sample of cells is fixed and permeabilized prior to contacting with the antibody against an ASRA protein.

6. The method of claim 1, wherein the asymmetrically self-renewing dividing cell is an undifferentiated cell.

7. The method of claim 1, wherein the asymmetrically self-renewing dividing cell is a tissue specific stem cell (TSSC).

8. The method of claim 7, wherein the TSSC is a hematopoietic stem cell (HSC) or a hair follicle stem cell (HFSC).

9. The method of claim 8, wherein the HSC is expanded for bone marrow transplantation or the HFSC is expanded for hair replacement therapy.

10. The method of claim 8, wherein the asymmetrically self-renewing dividing cell is obtained from a source selected from the group consisting of cord blood, bone marrow and mobilized peripheral blood.

11. The method of claim 10, wherein the asymmetrically self-renewing dividing cell is expanded ex vivo.

12. The method of claim 1, wherein the ASRA protein is a pattern-specific asymmetrically located cell-cycle specific protein (CCSP).

13. The method of claim 12, wherein the CCSP is selected from the group consisting of cyclin A, cyclin D1, cyclin E, CDKN1A, TK, Ki67, TS, DHFR and GAS-X proteins.

* * * * *